(12) United States Patent
Remelius

(10) Patent No.: US 11,150,318 B2
(45) Date of Patent: *Oct. 19, 2021

(54) SYSTEM AND METHOD OF CAMERA-LESS OPTICAL MOTION CAPTURE

(71) Applicant: Jebb Remelius, Pittsfield, MA (US)

(72) Inventor: Jebb Remelius, Pittsfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,835

(22) Filed: May 15, 2020

(65) Prior Publication Data

US 2020/0278417 A1    Sep. 3, 2020

Related U.S. Application Data

(63) Continuation of application No. 16/276,152, filed on Feb. 14, 2019, now Pat. No. 10,698,067.

(60) Provisional application No. 62/630,364, filed on Feb. 14, 2018.

(51) Int. Cl.
| | |
|---|---|
| *G01S 3/781* | (2006.01) |
| *G01P 13/00* | (2006.01) |
| *G01S 3/782* | (2006.01) |
| *A61B 5/11* | (2006.01) |
| *G01S 17/66* | (2006.01) |
| *G06K 9/00* | (2006.01) |
| *A61B 5/00* | (2006.01) |

(52) U.S. Cl.
CPC .............. *G01S 3/781* (2013.01); *A61B 5/1114* (2013.01); *A61B 5/1127* (2013.01); *G01P 13/00* (2013.01); *G01S 3/782* (2013.01); *G01S 17/66* (2013.01); *G06K 9/00335* (2013.01); *A61B 5/742* (2013.01); *A61B 5/7405* (2013.01); *A61B 5/7455* (2013.01); *A61B 2560/0223* (2013.01)

(58) Field of Classification Search
None
See application file for complete search history.

(56) References Cited

U.S. PATENT DOCUMENTS

2018/0329024 A1    11/2018 Send et al.

OTHER PUBLICATIONS

Heisig et al., "Fingernail Sensors and AI Can Help Clinicians to Monitor Health and Disease Progression"; IBM Blog, Healtcare; Posted Dec. 21, 2018; retrieved from: http://www.ibm.com/blogs/research/2018/12/fingernail-sensors/ on Feb. 5, 2019, 2 Pages.
Ortega et al., "A Miniaturized Two Axis Sun Sensor for Altitude Control of Nano-Satellites"; IEEE Sensors Journal; vol. 10, No. 10, Oct. 2010; pp. 1623-1632.

(Continued)

*Primary Examiner* — Michelle M Iacoletti
(74) *Attorney, Agent, or Firm* — DLA Piper, LLP (US)

(57) ABSTRACT

According to some embodiments, a motion tracker device can include a substrate and a plurality of light-direction detectors mounted on the substrate. Each light-direction detector may be configured to: detect, at two optically isolated points, the intensity of a light from a light source; generate a current signal representing the photodiode differential and proportional to the intensity of the light; and transmit the current signal to a computing device. Each of the plurality of light-direction detectors can be mounted on the substrate at an angle selected such that the computing device can use the transmitted signal to determine the motion of a motion tracker with six degrees of freedom.

14 Claims, 20 Drawing Sheets

(56) References Cited

OTHER PUBLICATIONS

Six Degrees of Freedom—Overview; ScienceDirect; Retrieved from the Internet: https://www.sciencedirect.com/topics/medicine-and-dentistry/six-degrees-of-freedom; Date Accessed: Feb. 11, 2019; 27 Pages.

Wang et al., "A Variable Self-powered Light Detection CMOS Chip with Real-Time Adaptive Tracking Digital Output Based on a Novel On-Chip Sensor"; Optics Express: Oct. 2017; 11 Pages.

Wang et al., CMOS Self-Powered Monolithic Light-Direction Sensor with Digitalized Output; Optics Letters; vol. 39. No. 9, May 1, 2014; pp. 2618-2621.

Wang et al., "On-Chip Sensor for Light Direction Detection"; Optics Letters; vol. 35, No. 22; Nov. 15, 2013; pp. 4554-4557.

SYSTEM AND METHOD OF CAMERA-LESS OPTICAL MOTION CAPTURE

PRIORITY

This application is a continuation of U.S. patent application Ser. No. 16/276,152, filed Feb. 14, 2019, which claims priority to U.S. Provisional Patent Application No. 62/630,364, filed on Feb. 14, 2018. All of the foregoing are incorporated herein by reference in their entireties.

FIELD OF INVENTION

This disclosure relates generally to motion-capture technology, and, more particularly, to a system for capturing, tracking and analyzing motion in six dimensions without the use of cameras.

BACKGROUND

Existing motion-capture systems may detect infrared (IR) signals with expensive digital cameras having one or more lenses. The IR signals may be emitted from active markers or a ring of LEDs surrounding each lens which cause light to be bounced off of retro-reflective passive markers affixed to the object being tracked. These motion-capture systems may require at least three cameras to be effective. Some systems operate with more than six cameras, and some systems are scaled up to even 300 cameras.

However, currently available motion-capture systems may only record three-dimensional (3D) positions of single points, describing an object's motion in left-to-right, up-and-down or forward-and-backward. Data with six degrees of freedom (6 DoF), including rotational movement about the x-, y- and z-axes, is often highly valuable for body position analysis in medicine, in virtual reality mechanics, and in reality-based animation, among other applications. In order to approximate 6 degrees of freedom, a motion-capture technician may currently need to apply and track three or more passive markers to get a single 6 DoF description.

Problems can occur with camera-based motion capture when the three markers are close together physically or have apparent angles, relative to individual cameras, that are very nearly the same. Further issues can arise if the cluster of markers is too far or too close to any of the cameras. Messy merging of these passive markers often results, which contaminates and degrades 6 DoF matrix data output. After recording data, each passive marker must be individually labeled, and picked-up again if momentarily dropped. Additionally, even when working with very accurate motion-capture data, animations produced from the captured data often get trapped in the "uncanny valley" where realism is not truly felt and audiences may react negatively. Part of today's failure to create realism occurs because the passive markers used to capture an actor's face may only yield 3 DoF data. For example, it may be physically impossible to provide enough adjacent markers to track features such as the curl of the lip in 6 DoF. There are hybridized motion-capture systems that pair passive markers with inertial sensors, but such systems may have increased complexity and suffer from so-called "double differential" errors.

SUMMARY

A system is needed to provide accurate and consistent six degrees of freedom motion-capture with equipment that is easy to manipulate and carry and doesn't degrade data by virtue of its size.

One aspect of the present disclosure is directed to a motion tracker device comprising a substrate and a plurality of light-direction detectors (LDD), each configured to detect, at two optically isolated points, the intensity of a light from a light source. The light-direction detectors may be configured to generate a current signal representing the photodiode differential and proportional to the intensity of the light, and to transmit the current signal to a computing device. Considering two of the plurality of light-direction detectors, these two light-direction detectors may be mounted on the substrate such that the angle of incidence of the light on the first and second light-direction detectors is different.

In some embodiments, the computing device may be configured to determine the motion of the motion tracker device with six degrees of freedom based on the current signals transmitted from the plurality of light-direction detectors. In some embodiments, each light-direction detector may comprise a microchip. In some embodiments, each light-direction detector may comprise a plurality of photodiodes optically isolated from one another by a stacked metallic layer. In some embodiments, each light-direction detector may be mounted on the substrate at an angle that may be not aligned with or parallel to the surface of the substrate. In some embodiments, each light-direction detector may be mounted on the substrate at an angle of 30 degrees or 60 degrees relative to the substrate. In some embodiments, the motion tracker may comprise a light emission source and the light emission source may a light-emitting diode (LED). In some embodiments, the light-direction detectors may be mounted on the substrate orthogonally to each other. In some embodiments, two of the plurality of light-direction detectors may be incorporated into a single microchip. In some embodiments, the motion tracker device may be configured to be mounted on a human fingernail. In some embodiments, the motion tracker device may comprise a second substrate, and a second plurality of light-direction detectors mounted on the second substrate, each configured to detect, at two optically isolated points, the intensity of a light from a light source. The light-direction detectors may be configured to generate a current signal representing the photodiode differential and proportional to the intensity of the light, and to transmit the current signal to a computing device. Considering two of the second plurality of light-direction detectors, these two light-direction detectors may be mounted on the second substrate such that the angle of incidence of the light on the first and second light-direction detectors may be different. The angle of first light-direction detectors relative to the first substrate may be different than the angle of the second light-direction detectors relative to the second substrate. The first plurality of light-direction detectors may be connected to the second light-plurality of light-direction detectors such that the second substrate may be sandwiched between the two layers of light-direction detectors. The light-direction detectors of the first plurality of light-direction detectors may be mounted on the first substrate at an angle of 60 degrees relative to the first substrate and the light-direction detectors of the second plurality of light-direction detectors may be mounted on the second substrate at an angle of 30 degrees relative to the second substrate.

Another aspect of the present disclosure is directed to a system for tracking light comprising a substrate and a plurality of motion trackers mounted at different positions on the substrate. Each motion tracker may be comprised of a second substrate and a plurality of light-direction detectors (LDD), each configured to detect, at two optically isolated points, the intensity of a light from a light source. The light-direction detectors may be configured to generate a current signal representing the photodiode differential and proportional to the intensity of the light; and to transmit the current signal to a computing device. Considering two of the plurality of light-direction detectors, these two light-direction detectors may be mounted on the substrate such that the angle of incidence of the light on the first and second light-direction detectors is different.

In some embodiments, the computing device is configured to determine the motion of the motion tracker device with six degrees of freedom based on the current signals transmitted from the plurality of light-direction detectors. In some embodiments, each light-direction detector comprises a microchip. In some embodiments, two of the plurality of light-direction detectors are incorporated into a single microchip.

BRIEF DESCRIPTION OF THE DRAWINGS

The accompanying drawings, which are incorporated in and constitute a part of this specification, illustrate an implementation of the invention and, together with the description, explain the goals, advantages and principles of the invention. Corresponding reference numerals indicate corresponding parts throughout the several views of the drawings. In the drawings.

DETAILED DESCRIPTION

In the following description, numerous specific details are set forth regarding the systems and methods of the disclosed subject matter and the environment in which such systems and methods may operate in order to provide a thorough understanding of the disclosed subject matter. It may be apparent to one skilled in the art, however, that the disclosed subject matter may be practiced without such specific details, and that certain features, which are well known in the art, are not described in detail in order to avoid unnecessary complication of the disclosed subject matter. In addition, it may be understood that the embodiments provided below are exemplary, and that it may be contemplated that there are other systems and methods that are within the scope of the disclosed subject matter.

Figure 1A:
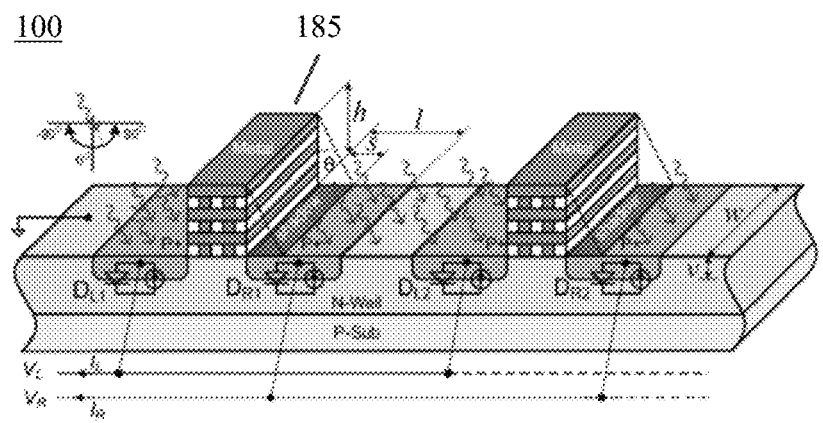
FIG. 1A is a diagram of an exemplary light-direction detector.
Figure 1B:
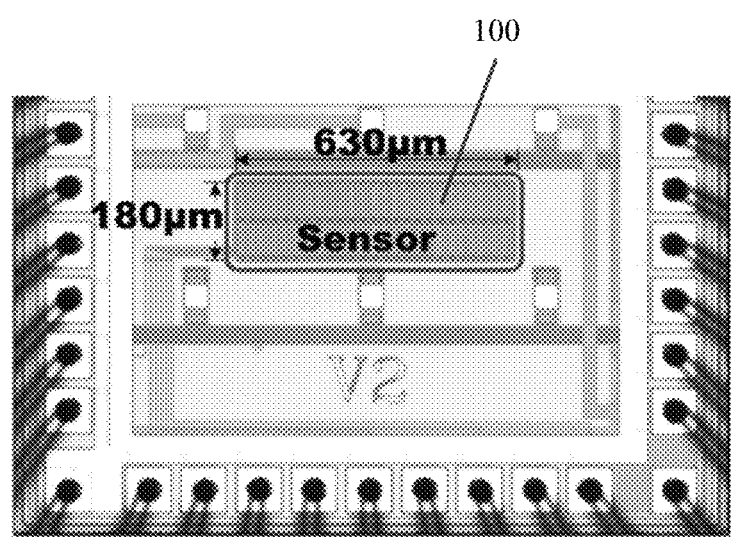
FIG. 1B is a top view of an exemplary light-direction detector mounted on a Complementary Metal Oxide Semiconductor (CMOS) chip as the substrate.

The term "light-direction detector," as used herein, refers to any type of optical sensor configured to detect the direction of light from a light source relative to the detector. One exemplary embodiment of such a light-direction detector is discussed in "On-chip sensor for light direction detection", by Hongyi Wang, Tao Luo, Hongjiang Song, and Jennifer B. Christen, Optics Letters 38, 4554 (2013) incorporated herein by reference. FIGS. 1A and 1B provide illustration of the Wang device. The action of the particular light-direction detector embodiment illustrated in FIGS. 1A and 1B is best described by Wang,

[t]he sensor consists of 50 basic cells connected in parallel. FIG. [1A] shows the structure of two basic cells. The essential feature of this sensor is created by stacking all metal layers, contact, and vias available in the process to create on-chip walls as optical baffles [102]. Two identical photodiodes 104 are located on opposite sides of the wall [185]. When the light comes from directly above the wall [185], the two photodiodes are illuminated equally and produce the same currents. When the light comes from one side above the wall [185], the wall [185] blocks part of the light from the opposite photodiode, which therefore produces less current than the other photodiode. The difference of these two currents depends on the angle of the incident light. It is possible to calculate the angle based on these two currents. id.

Figure 1C:
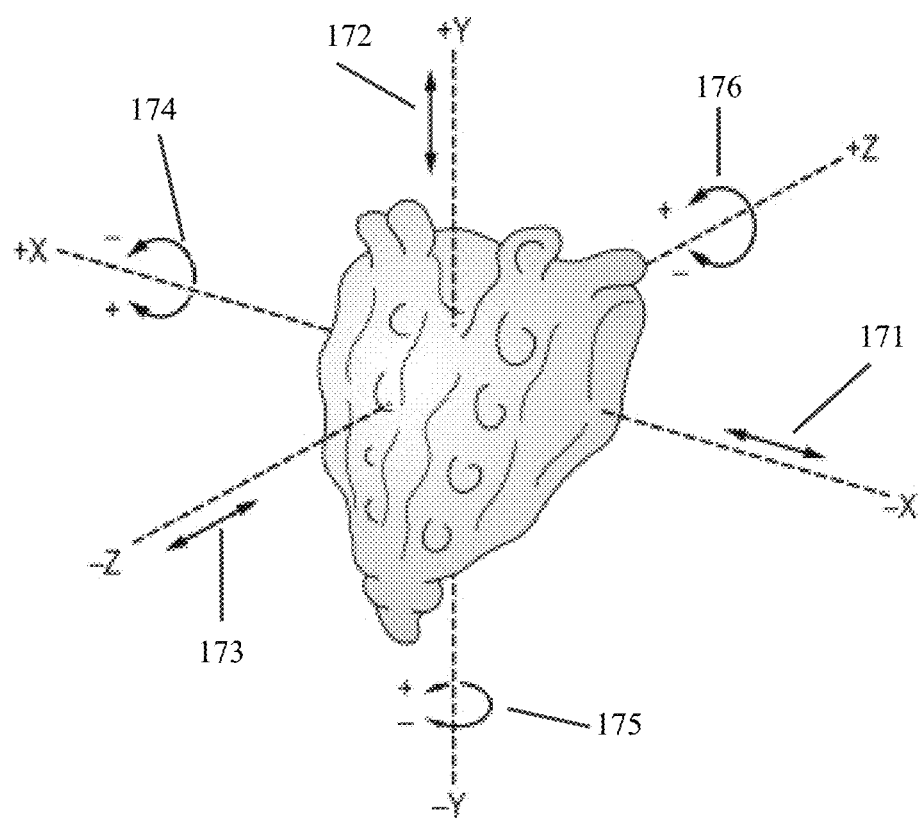
FIG. 1C is a diagram showing 6 degrees of freedom of motion for an object.

The term "six degrees of freedom (6 DoF)," as used herein, refers to six potential movements made by a body in space. FIG. 1C illustrates this motion as: side-to-side movement 171 (along the x-axis); up and down movement 172 (along the y-axis); forward and backward movement 173 (along the z-axis); turning about an x-axis movement 174 pitch); turning about a y-axis movement 175 (yaw); and turning about a z-axis movement 176 (roll) (From *A suspensory system for the sacrum in pelvic mechanics: biotensegrity*. SM Levin, in Movement, Stability & Lumbopelvic Pain (Second Edition), 2007. Found online at https://www.sciencedirect.com/topics/medicine-and-dentistry/six-degrees-of-freedom, last visited Feb. 8, 2019.).

The present disclosure describes a camera-less optical motion-capture system. Wearable sensors may measure six degrees of freedom (6 DoF) of motion of the object to which they are attached. This may be made possible by placing light emitting diode (LED) lights, in groups or as single light sources, around a room, for example. Each LED array may be controlled (e.g., by a computer system) to flash in a particular pattern with other individual LEDs or groups of LEDs in a particular pattern (e.g., circular, spiral or linear). A particular group of LEDs may include two, three, four, or greater numbers of LEDs. The light source of a single LED or LED array may be estimated as a point source. By presenting lights that flash in linear arrangements, the angular relationship between light source and sensor may give additional data on 6 DoF of the motion of the sensor. By increasing the number of lights flashed at a specific location, the distance from the light source to the sensor may be calculated.

In some embodiments, the system may include a light source located directly on a 6 DoF sensor. In some embodiments, the camera-less motion-capture system may be hybridized by combining it with a camera-based motion-capture system measuring only 3 DoF. Hybridizing the camera-less system with a camera system for motion capture may be made possible by hardware or software additions that enable serial flashes of LED rings that may surround each motion-capture camera and typically flash simultaneously with the shutter of the camera. With the camera LED rings flashing in a serial sequence, sensors may compute 6 DoF relative to statically mounted cameras. With patterned flashing of the LED on the 6 DoF sensor, an identifying signature of each sensor may be transmitted to the cameras, and the sensors' 3 DoF positions may be constructed in the standard motion-capture process. Hybridizing the camera-less system with a camera-based system may give resiliency to the data by adding redundancy and double checks on the computed results.

Figure 2:
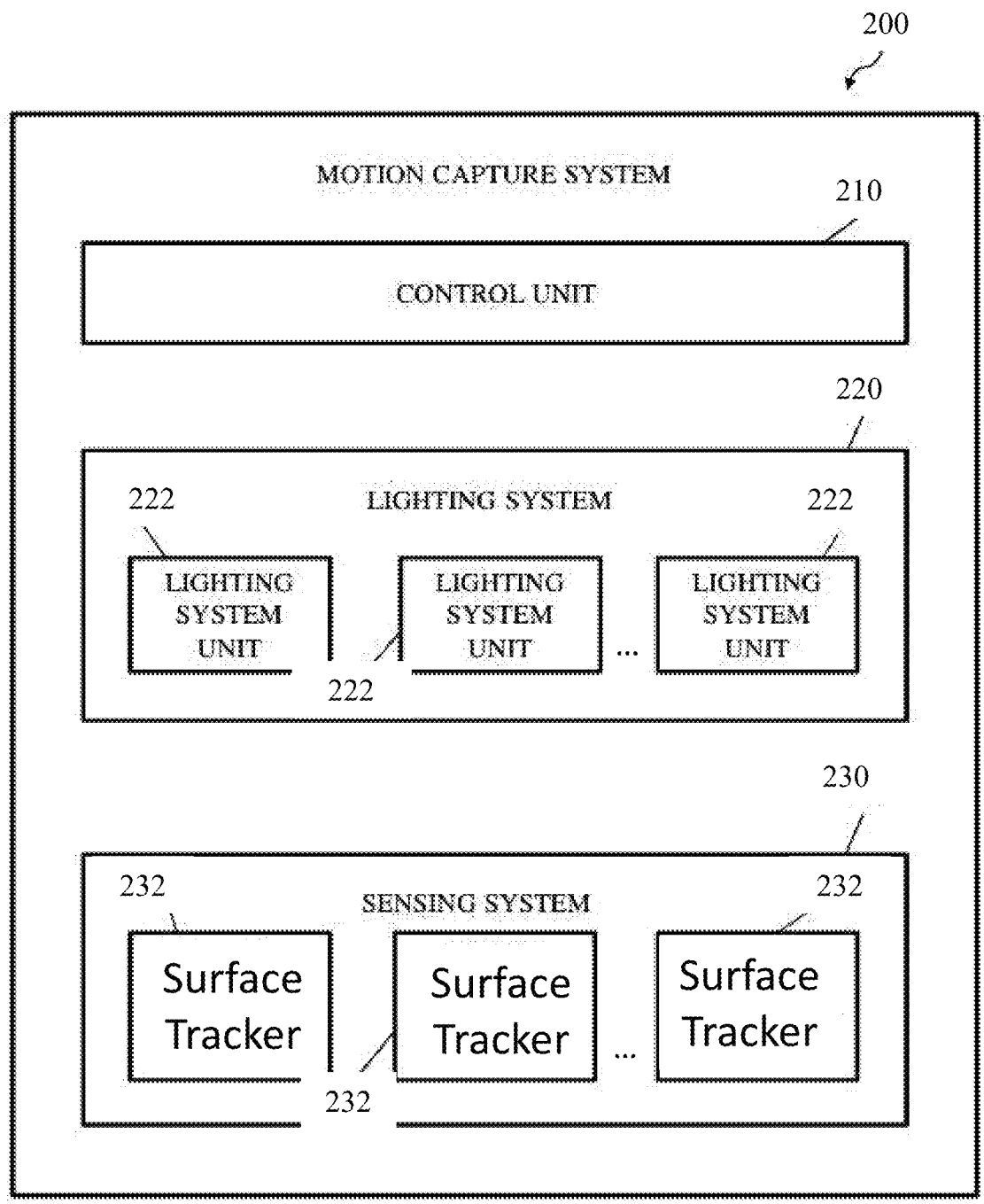
FIG. 2 is a block diagram illustrating a motion capture system, according to some embodiments, according to some embodiments of the present disclosure.

FIG. 2 shows a block diagram of a motion-capture system 200, according to some embodiments of the present disclosure. The system may be described as a camera-less optical motion capture. In some embodiments, the system may include a computer system 210, a lighting system 220 and a sensing system 230. The computer system 210 may control the operation of the lighting system 220 and collect data from the sensing system 230. The computer system may calculate motion or position data of the target based on the collected data. The lighting system 220 may include one or more lighting system units (LSUs) 222 which may be controlled by the computer system 210 to flash in a known sequence alone or in clusters of LSUs as close as physically possible as adjacent pairs, triads, quads, or greater numbers. While FIG. 2 shows 3 LSUs, a person of ordinary skill in the art would understand that fewer or more LSUs can be used in some embodiments of the present disclosure and that the particular number of LSUs may be selected based on the requirements for a given application.

The sensing system 230 may include one or more motion trackers 232 which may determine the light intensity at the its surface and send readings to computer system 210 where the angle of incidence and motion can be calculated. The sensing system 230 may include any number of motion trackers 232. While FIG. 2 shows 3 motion trackers, a person of ordinary skill in the art would understand that fewer or more motion trackers can be used in some embodiments of the present disclosure and that the particular number of motion trackers mage be selected based on the requirements for a given application.

The lighting system 220 may include a number of lighting-system units (LSUs) 222 connected to a computer system, with wires or wirelessly, and configured to emit light. In some embodiments, the number of the LSUs may be between 4 and 100 or more. Each LSU 222 may have a wide angle of light dispersion (>180 degree hemispherical) and may be arranged such that its light saturates a rectangular volume or area within which motion capture of movement may occur. The wide angle of light dispersion from an LSU 222 may enable motion capture by motion trackers located near the walls of the room. The LSUs 222 may emit light in the spectrum from violet to infrared (e.g., having a wavelength of 400 nm to 1.2 mm). Each discrete LSU may include a number of LEDs, Wi-Fi, digital communication equipment, a battery or some combination of these elements. In some embodiments, the number of LEDs may be 40 or more. The powering of all or a select number of LEDs on each LSU may be controlled by the computer system to illuminate with a specific duration and frequency.

Figure 14:
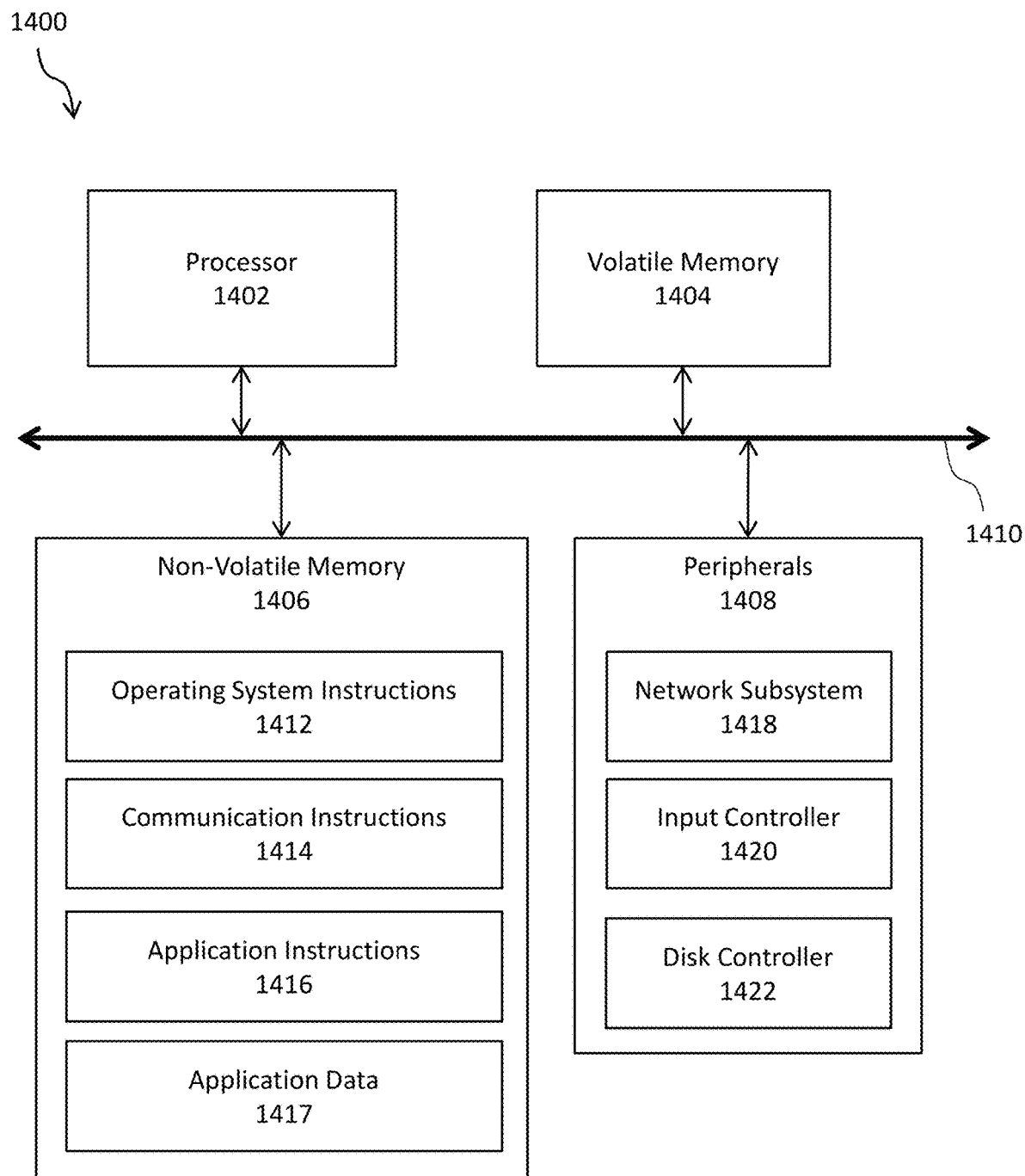
FIG. 14 is a block diagram of an exemplary computer system, according to some embodiments of the present disclosure.

FIG. 14 is a block diagram of an exemplary computer system 1400, according to some embodiments of the present disclosure. The computer system 1400 may be implemented on any electronic device that runs instructions, including without limitation microprocessors, personal computers, servers, smart phones, media players, electronic tablets, game consoles, email devices, etc. In some implementations, the computer system 1400 may include one or more processors 1402, volatile memory 1404, non-volatile memory 1406, or one or more peripherals 1408. These components may be interconnected by one or more computer buses 1410.

A processor 1402 may use any known processor technology, including but not limited to graphics processors and multi-core processors. Suitable processors for the execution of a program of instructions may include, by way of example, both general and special purpose microprocessors, and the sole processor or one of multiple processors or cores, of any kind of computer. A bus 1410 may be any known internal or external bus technology, including but not limited to ISA, EISA, PCI, PCI Express, NuBus, USB, Serial ATA or FireWire. Volatile memory 1404 may include, for example, SDRAM. A processor 1402 may receive instructions and data from a read-only memory or a random access memory or both. The essential elements of a computer may include a processor for executing instructions and one or more memories for storing instructions and data.

Examples of non-volatile memory 1406 may include semiconductor memory devices, such as EPROM, EEPROM, and flash memory devices; magnetic disks such as internal hard disks and removable disks; magneto-optical disks; and CD-ROM and DVD-ROM disks. Non-volatile memory 1406 may store various computer instructions including operating system instructions 1412, communication instructions 1414, application instructions 1416, and application data 1417. Operating system instructions 1412 may include instructions for implementing an operating system (e.g., Mac OS®, Windows®, or Linux). The operating system may be multi-user, multiprocessing, multitasking, multithreading, real-time, and the like. Communication instructions 1414 may include network communications instructions, for example, software for implementing communication protocols, such as TCP/IP, HTTP, Ethernet, telephony, etc. Application instructions 1416 may include instructions for controlling LSUs or motion trackers or for collecting, storing, retrieving or analyzing light- or motion-related data.

Peripherals 1408 may be included within the computer system 1400 or operatively coupled to communicate with the computer system 1400. Peripherals 1408 may include, for example, network interfaces 1418, input devices 1420, storage devices 1422, or display devices. Network interfaces may include Ethernet or WiFi adapters or physical wiring connections. Input devices 1420 may be any known input device technology, including but not limited to a keyboard (including a virtual keyboard), mouse, track ball, or touch-sensitive pad or display. Storage devices 1422 may include mass storage devices for storing data files (e.g., magnetic disks, internal hard disks, removable disks, magneto-optical disks, optical disks).

The computer system may store the 3D coordinate location of each controlled LSU as determined by a calibration procedure, described by example below. In some embodiments, the volume or area encompassed may be scaled from under 1 cubic meter up to or exceeding 5,000 cubic meters or more by adding or removing LSUs. In some embodiments, the LSUs 222 may be affixed on walls ceiling, floors, or may be mounted on free standing poles or tripods.

Figure 3A:
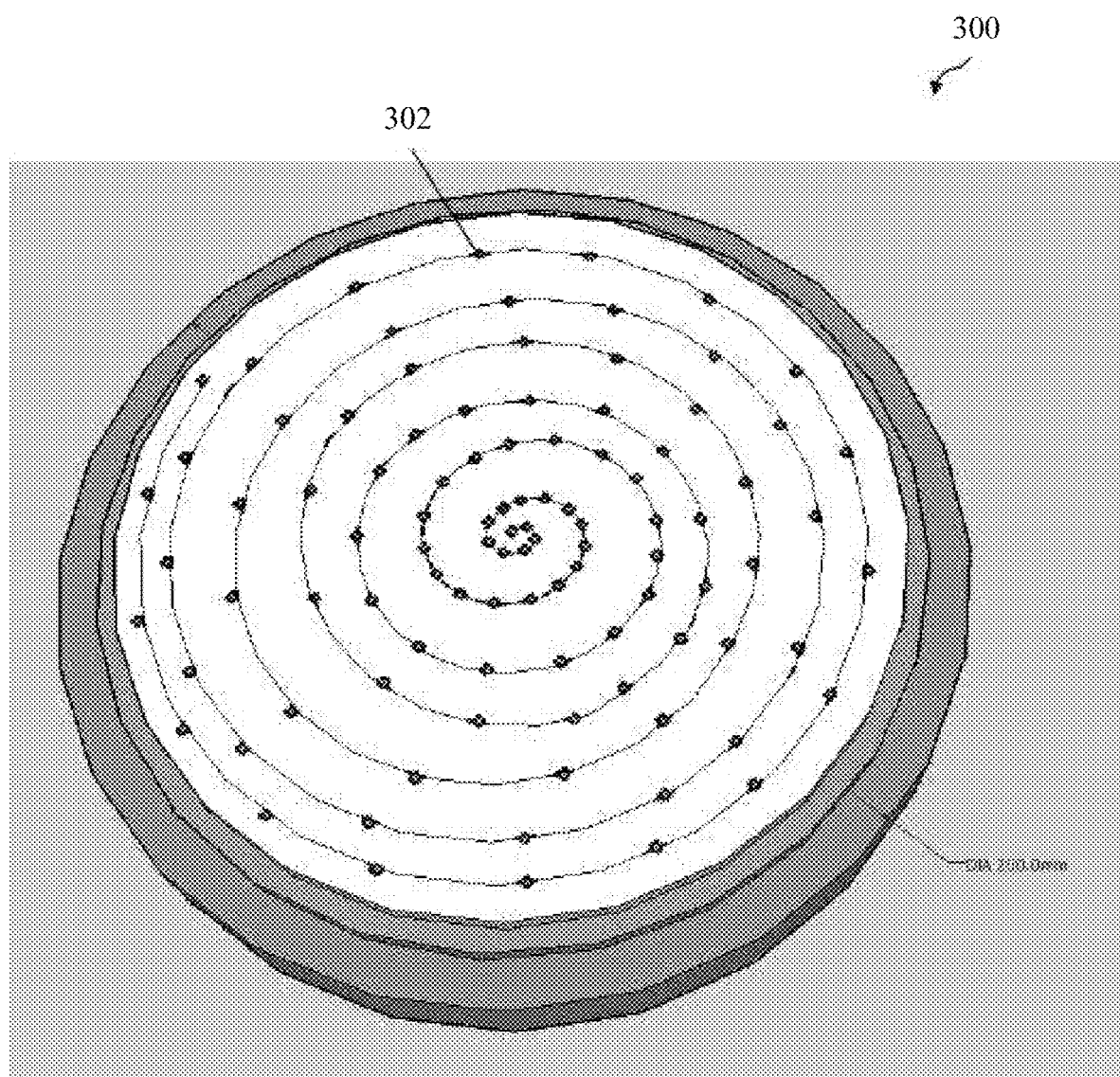
FIG. 3A is a perspective view of a lighting-system unit (LSU), according to some embodiments of the present disclosure.

FIG. 3A shows an exemplary LSU 300 with a plurality of light emitting diodes (LEDs) 302 arranged in a spiral layout, according to some embodiments of the present disclosure. In some embodiments, the LEDs may also be arranged in a concentric circular layout.

Figure 3B:
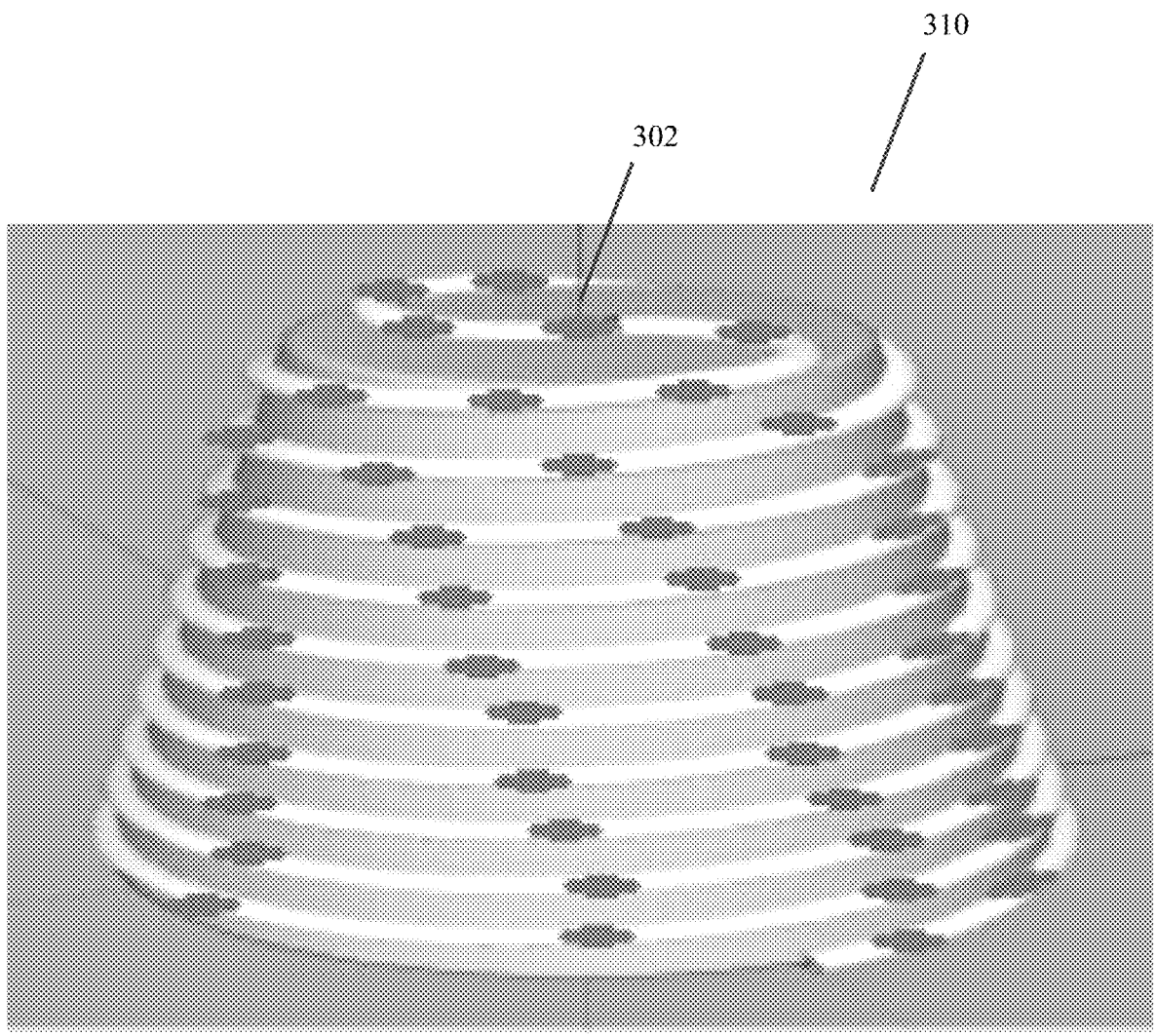
FIG. 3B is a perspective view of an LSU, according to some embodiments of the present disclosure.

FIG. 3B shows an exemplary LSU 310 with a plurality of LEDs 302 arranged in a spiral conical layout, according to some embodiments of the present disclosure.

Figure 3C:
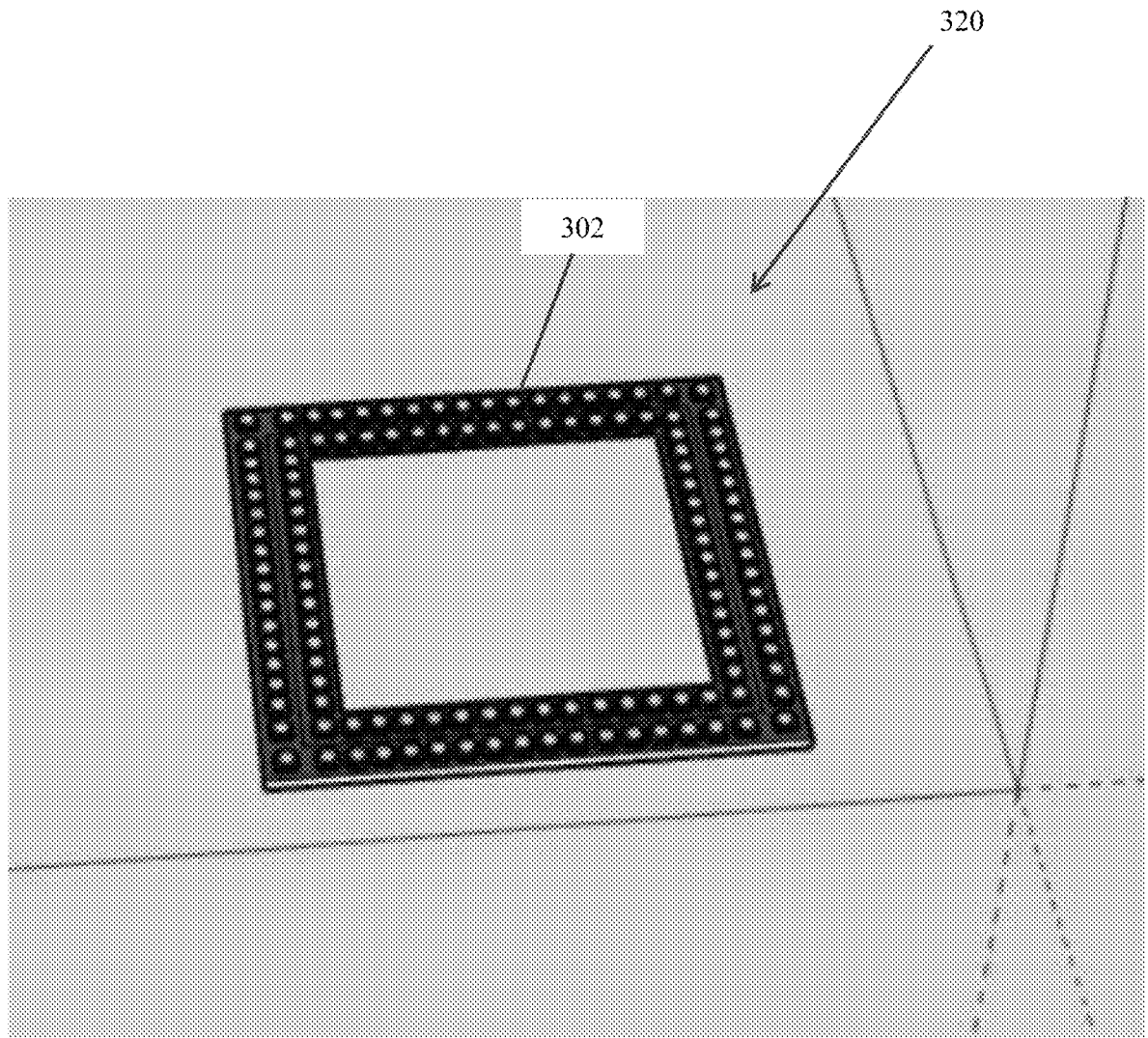
FIG. 3C is a perspective view of an LSU, according to some embodiments of the present disclosure.

FIG. 3C shows an exemplary LSU 320 with a plurality of LEDs 302 arranged in a linear layout, according to some embodiments of the present disclosure. The LSU may be very small (e.g., a few millimeters long) or very large (e.g., several feet long). In some embodiments, the LEDs may be arranged in a number of rows (e.g., 3, 4, 5 rows or more) with any number of LEDs in each row (e.g., 20, 40, 50 or more). In some embodiments, the LEDs may be arranged in rows about the perimeter of a rectangle where the center of the rectangle may be open as depicted in FIG. 3C.

Figure 3D:
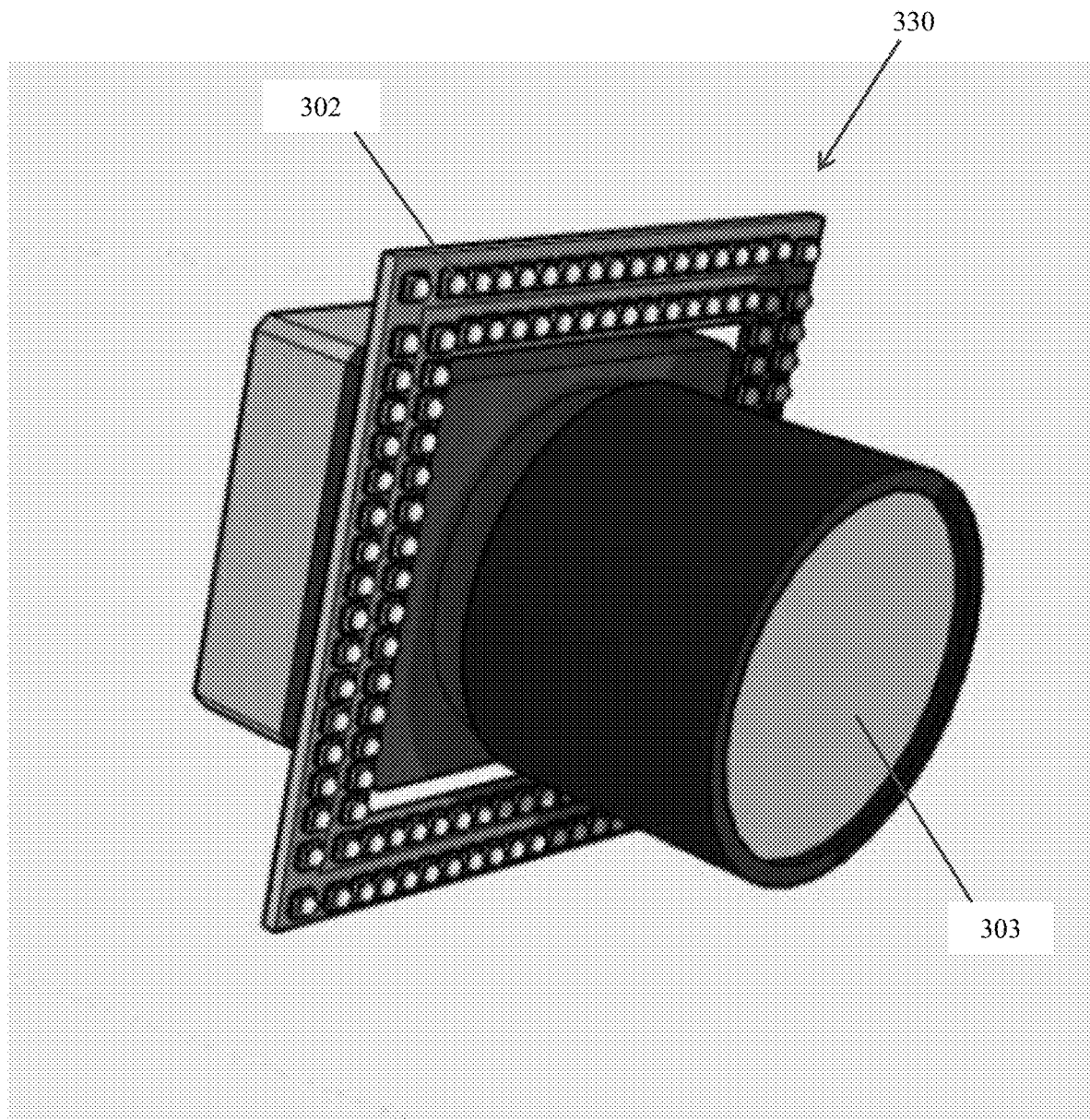
FIG. 3D is a perspective view of an LSU mounted on a generic motion-capture camera, according to some embodiments of the present disclosure.

FIG. 3D shows an exemplary LSU 330 with a plurality of LEDs 302 arranged in a quadrilateral arrangement (similar to that shown in FIG. 3C), and mounted to a generic motion-capture camera 303 according to some embodiments of the present disclosure. In some embodiments, LEDs in a lighting system unit may be arranged in another layout.

Figure 4:
FIG. 4 is a view of an exemplary lighting system, according to some embodiments of the present disclosure.

FIG. 4 shows an exemplary lighting system 400 including four LSUs 420. This type of exemplary lights system 400 may include as few as one LSU 420 or as many as the stand apparatus can support. In some embodiments, the LSUs 420 may be mounted on a supporting stand or a mobile tripod 402 for specialized motion capture, according to some embodiments of the present disclosure.

Figure 5A:
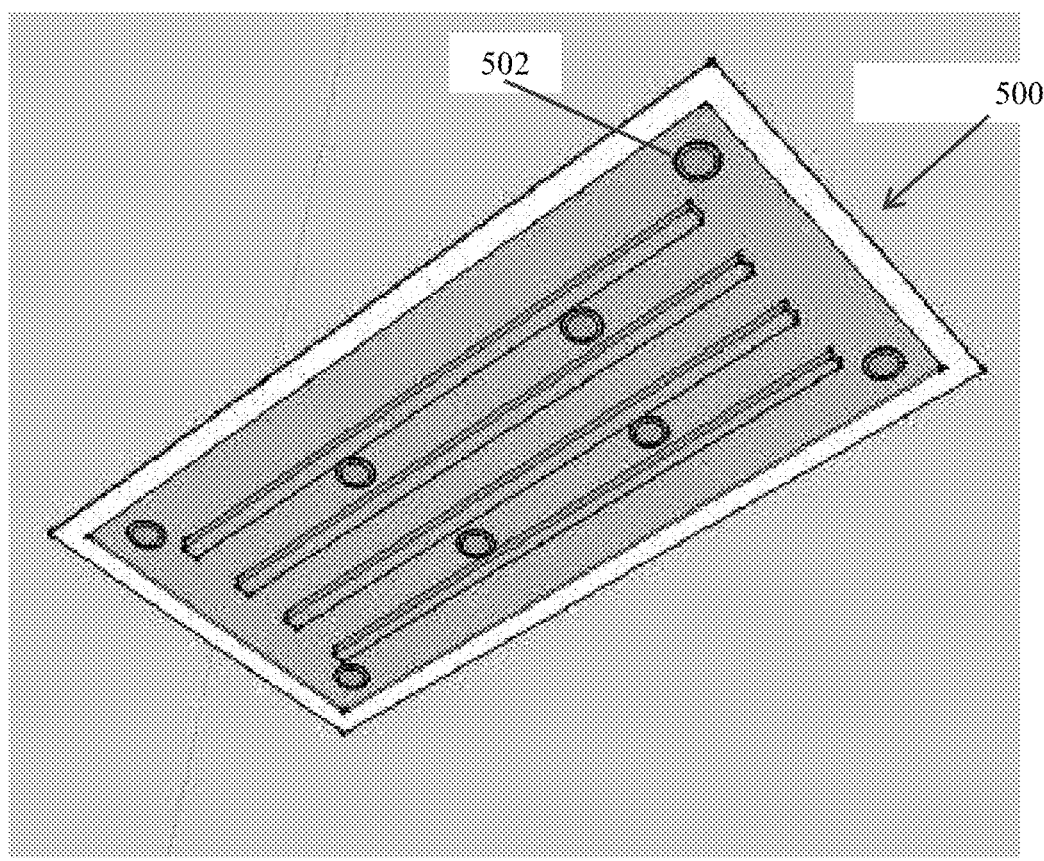
FIG. 5A is a view of an exemplary lighting system, according to some embodiments of the present disclosure.
Figure 5B:
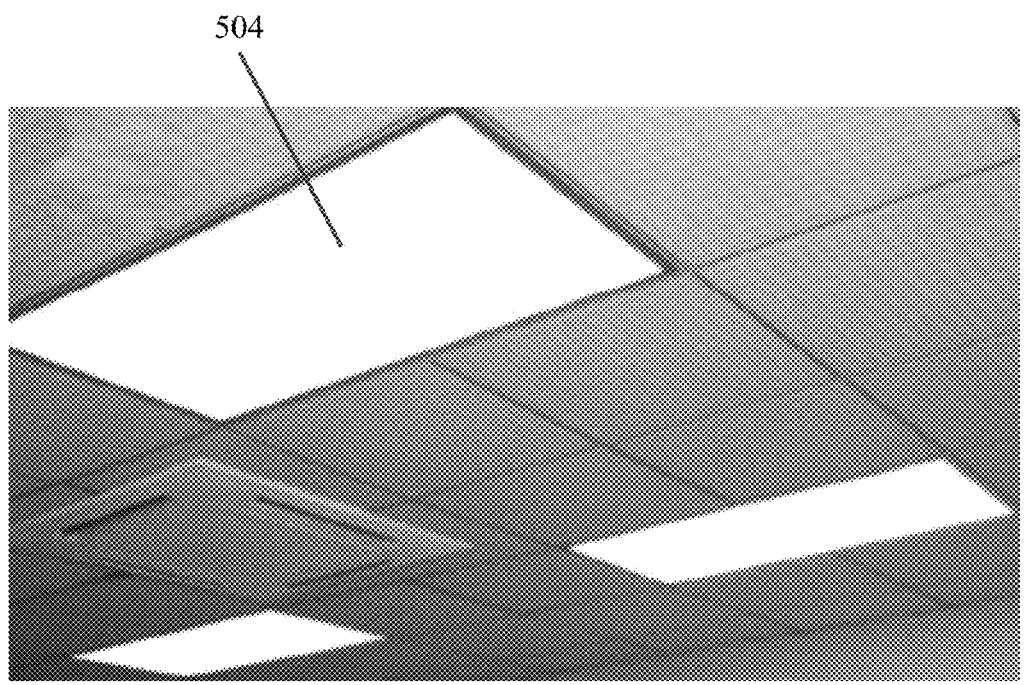
FIG. 5B is another view of an exemplary lighting system, according to some embodiments of the present disclosure.

FIG. 5A show an exemplary layout of an LSU 500, according to some embodiments of the present disclosure. The LEDs 502 may be arranged in panels of room lights. For example, the LEDs 502 may be mounted in a standard 4'×2' recessed ceiling panel lighting fixture. FIG. 5B shows an exemplary embodiment of a standard 4'×2' ceiling panel lighting fixture 504.

Figure 6:
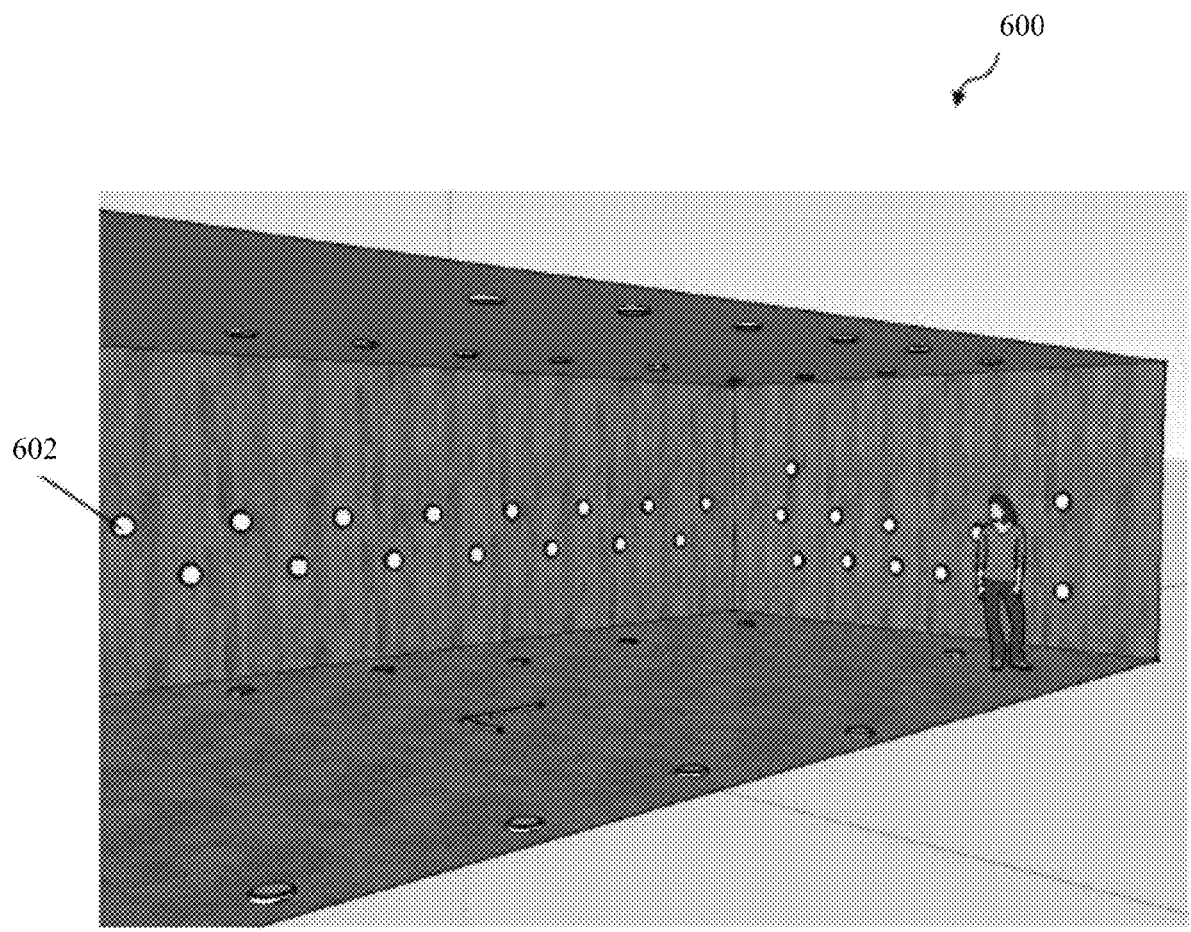
FIG. 6 is a view of an exemplary motion capture lab, according to some embodiments of the present disclosure.

FIG. 6 shows an exemplary layout of a motion-capture lab 600, according to some embodiments of the present disclosure. Any number of LSUs 602 may be mounted on the walls, floors and ceilings of such a motion-capture lab 600.

Referring to FIG. 7, a motion tracker 700 may generally comprise two or more light-direction detectors 702 mounted on a substrate 703. Each light-direction detector 702 may be configured to detect, at two optically isolated points, the intensity of a light from a light source, to generate a current signal representing the photodiode differential and proportional to the intensity of the light, and to transmit the current signal to a computing device. The light-direction detectors 702 may be mounted on the substrate at an angle that is not aligned with or parallel to each other. Each light-direction detector 702 may be mounted on the substrate at an angle that is not aligned with or parallel to the surface of the substrate. One light-direction detector 702 may be mounted on the substrate such that the angle of incidence of the light on that light-direction detector is different that the angle of incidence of the light on one other of the light-direction detectors 702 attached to the same substrate. The mounting of the light-direction detectors 702 at these angles may allow the motion of a motion tracker to be determined with six degrees of freedom. This mounting of the light-direction detectors 702 at positions yielding different angles of incidence is critical because the varied angles increases the breadth of the light receptivity of the motion tracker and the data available from the sensors, thus allowing the 6 DoF analysis.

Each light-direction detector 702 may be configured as a microchip capable of mounting on the substrate, similar to the prior art light-direction detector shown in FIGS. 1A and 1B and discussed above.

Figure 7A:
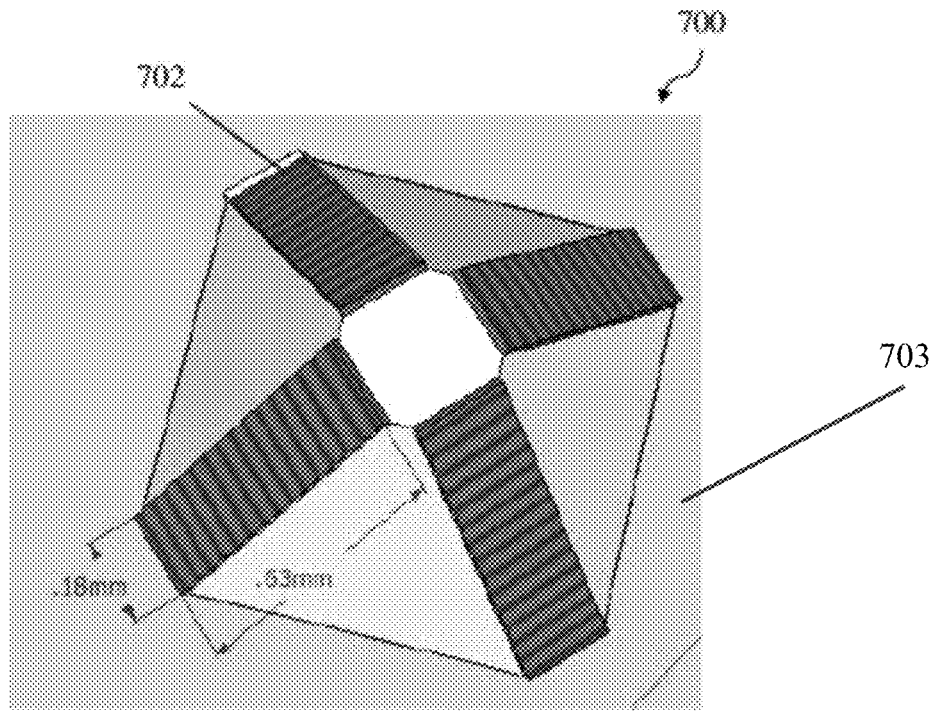
FIG. 7A is a view of an exemplary motion tracker, according to some embodiments of the present disclosure.

The light-direction detectors 702 may be mounted to the substrate at 45 degrees to the plane of the substrate. FIG. 7A shows a motion tracker 700 with 4 light-direction detectors 702 angled at 45 degrees to the horizontal substrate plane, combined to give a sensitivity hemisphere of approximately 200-degree, according to some embodiments of the present disclosure. As shown in FIG. 7A, each light-direction detector 702 may have a width of 0.18 mm and a length of 0.63 mm. In some embodiments, the light-direction detectors 702 may have other dimensions.

Figure 7B:
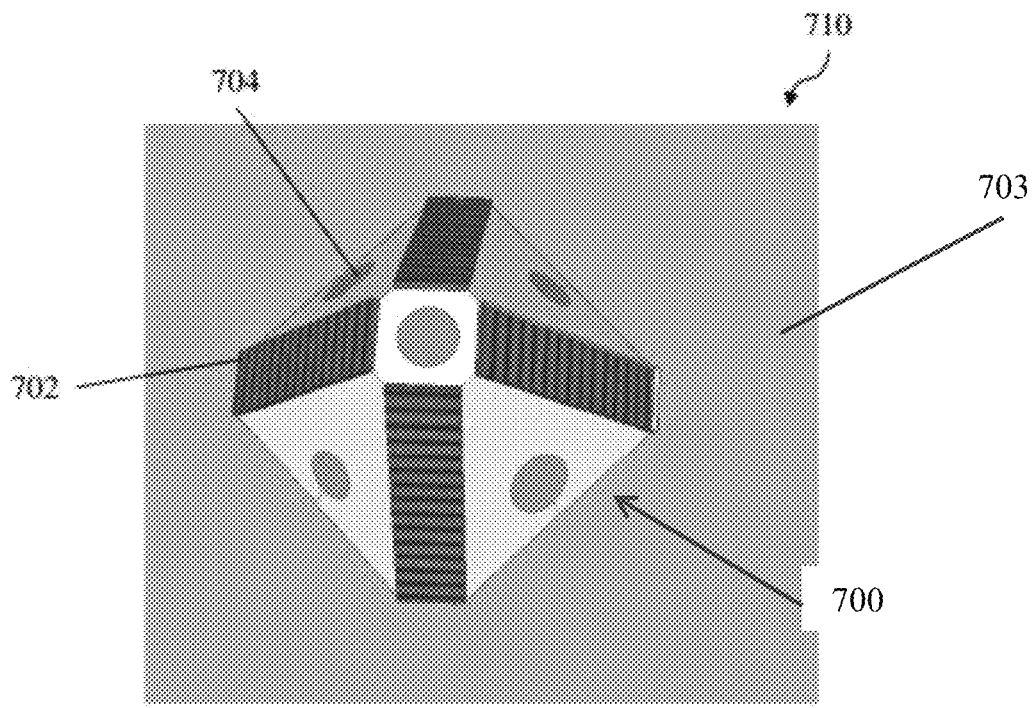
FIG. 7B is another view of an exemplary motion tracker, according to some embodiments of the present disclosure.

FIG. 7B shows a motion tracker unit 710 with 4 light-direction detectors 702 angle at 60 degrees to the horizontal plane, according to some embodiments of the present disclosure. The light-direction detector 702 detects light direction in one direction (perpendicular to the chip long axis), thus for a two-dimensional angle, two light-direction detectors 702 may be paired at orthogonal orientation relative to each other. If the light-direction detector 702 has a maximal angular detection range of 110 degrees, (55 degrees left and right of perpendicular to the light-direction detector), the final design of the motion tracker may be comprised of a 2 pairs of light-direction detectors, offset in angle to increase angular detection range to 180 degrees or greater. If further angular range above a 180-degree hemisphere were deemed necessary, additional pairs of light-direction detectors 702 may be fabricated onto the motion tracker. Other embodiments may have the light-direction detectors 702 mounted at different angles relative to the substrate, such as 15 degrees, 30 degrees, 60 degrees, or any other angle deemed necessary.

The motion tracker may include a light emission source. The light emission source may be an LED bulb or any other type of light emitter known in the art. FIG. 7B shows a motion tracker unit 710 with 5 LED bulbs 704, according to some embodiments of the present disclosure. The motion tracker may be equipped with a LED fabricated adjacent to the array of light-direction detectors 702 in a single device. The primary location of an LED 704 may be the top of the pyramid of light-direction detectors, and secondary locations radial from the center point along 45-degree directions relative to the primary coordinate system of the paired light-direction detectors. These light emission sources on the motion tracker allow relative Tracker-to-Tracker 6 DoF to be directly computed, even without being within an LSU. This would allow motion detection from any one motion tracker to another (e.g., from eyeglass frame to smart phone, from vehicle to vehicle, from vehicle to structure). The light emission source may also assist in locating the motion trackers.

The light-direction detectors 702 may be integrated circuit chips mounted to any suitable substrate 703 type known in the art, such as a CMOS chip. Two light-direction detectors 702 may be formed in the same chip and mounted to a substrate 703 as a single unit.

The motion tracker may be configured to be mounted to any type of wearable or movable device. Such devices may include tripods, selfie sticks, brackets, eyeglasses, fingernails, smartphones, or any other suitable device.

Figure 7C:
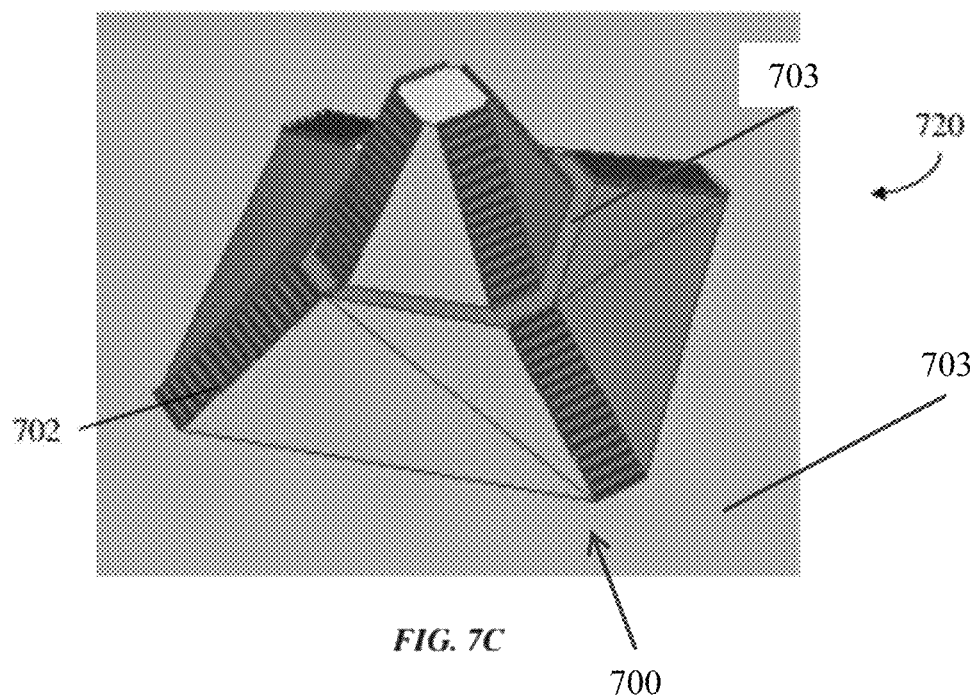
FIG. 7C is another view of an exemplary motion tracker, according to some embodiments of the present disclosure.

In an alternative embodiment, the motion tracker device may comprise two substrates 703 and two light-direction-detector layers. FIG. 7C shows an exemplary embodiment having a motion tracker unit 720 with two light-direction-detector layers. The each layer 704 may comprise two or more light-direction detectors 702 mounted to a substrate 703. In each layer, one light-direction detector 702 may be mounted on the substrate such that the angle of incidence of the light on that light-direction detector is different that the angle of incidence of the light on one other of the light-direction detectors 702 attached to the same substrate.

The mounting of the light-direction detectors 702 at these angles may allow the motion of a motion tracker to be determined with six degrees of freedom. This mounting of the light-direction detectors 702 at positions yielding different angles of incidence is critical because the varied angles increases the breadth of the light receptivity of the motion tracker and the data available from the sensors, thus allowing the 6 DoF analysis.

The light-direction detectors of the first layer may be mounted to the first substrate at an angle that is not aligned with and not parallel to the substrate (60 degrees in FIG. 7C). The light-direction detectors 702 of the second layer may be mounted to a second substrate 706 at an angle that is not aligned with and not parallel to the substrate (30 degrees in FIG. 7C). Further, the angle of the light-direction detectors of the first layer relative to the first layer's substrate may be different that the angle of the light-direction detectors of the second layer relative to the second layer's substrate. As shown in FIG. 7C, the two light-direction-detector layers 704 and 705 may be mounted on top of one another such that the second substrate 706 is sandwiched between the two layers. Configurations with different angles of the light-direction detectors 702 relative to the substrate increase the overall breadth of light angles that can be detected by the motion tracker. The different LDD-to-substrate angles of the two layers is critical because the combination of these different angles increases the breadth of the light receptivity of the motion tracker and the data available from the sensors, thus allowing the 6 DoF analysis. The combination in the exemplary embodiment of FIG. 7C may result in a 230-degree hemisphere of light detecting sensitivity. Other combinations of angles are possible and may be selected to achieve the desired angular end result as would be understood in the art. Additionally, overlapping angular detection ranges may increase precision and accuracy of the motion tracker, such that the increase in complexity of the light-direction detector 702 may be a worthwhile tradeoff for the increased complexity of analysis. Increased precision and accuracy may also be obtained through multiple discrete readings of direction by separate light-direction detectors 702 while referencing a single LSU.

Figure 7D:
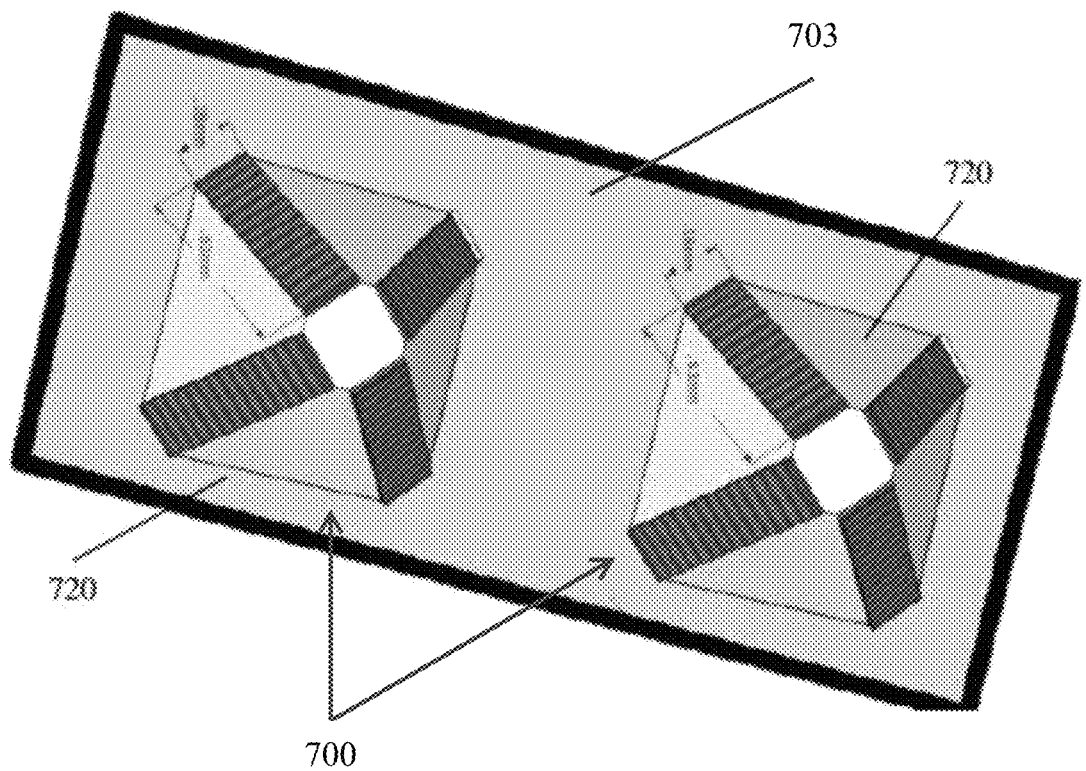
FIG. 7D is another view of an exemplary motion tracker, according to some embodiments of the present disclosure.

In an alternative embodiment, multiple motion tracker devices may be mounted to a single substrate 703. FIG. 7D shows a pair of motion tracker units 720 attached to a single rigid substrate 703, according to some embodiments of the present disclosure. The angles of the light-direction detectors 702 may be the same in each motion tracker device mounted to the substrate or different motion trackers may have different angles.

In order to perform calculations on the 6 DoF data of a motion tracker, each LSU of the lighting system must have known 3D coordinates. The precise coordinates of each light unit may be determined through a calibration process. To calibrate the motion-capture system, a calibration frame consisting of three motion trackers at a known and precise physical spacing may be placed in the area where most of the lighting system units will be pointed or visible. The precision calibration frame may have a known geometry that allows a mathematical triangulation of each lighting system unit in turn.

The lighting computer system may record and transmit time-stamped data describing the timing of power on and off events for each LSU. These events may occur at assigned times. In some embodiments, each LSU may be turned on for as little as 20 microseconds in a set sequence. There may be no delay between one unit turning off and the next turning on. The number of LSUs grouped in the lighting system may determine the cycle time (for instance 50 LSUs may give a 100 Hz cycle time). Any number of LEDs may be turned on during the unit's active time in each cycle, but may be grouped into sets that illuminate at the same time. Each sequential group size may get larger as the distance from the center point increases. Group sizes may increase from 1 (center point), next 2, next 4, next 8, next 16, next 32 or similar group-size growth trend. The center most LED may be powered on during each cycle, and additional numbers of LEDs may activate in sequence following adjacent neighbor LEDs in the spiral arrangement. The lighting of LEDs on an LSU may be patterned to emulate a point source of light at varying intensities. When the motion tracker is close to the LSU in 3D space, one central LED may be lit on that LSU, and as the motion tracker moves farther from an LSU, more lights may be turned on, and the LSU may still be perceived as a point light source by the system. The number of LEDs turned on at each unit's designated time point may be adjusted via system optimization commencing at the initiation of the lighting system. Initial cycles of the units may initialize with all LEDs illuminating simultaneously, and the number of LEDs illuminated may be reduced to lower light intensity from most those that are most distal on the spiral to those most proximal relative to the center point of the spiral on each unit, or by turning on and off expanding concentric rings in a circular arrangement of LEDs. The reduction in light output serves as a signal of the distance to the object the lighting system may be illuminating. One quiescent period of 20 microseconds may be incorporated into the cycle of powering the LSUs in order to take a background reading of ambient light conditions (sunlight, room lights or other).

When an LSU is formed into linear segments of LEDs (single line, square or rectangular quadrilateral), the LEDs may flash in a sequence such as: top row, bottom row, left row, then right row. The flashing may be organized to create unique shadow patterns on the light-direction detectors of each motion tracker. These unique shadows are due to the physical distance from left to right LEDs, and top to bottom LEDs. The location and linear equation of each segment may be taken from the calibration operation and stored in software, and these LSUs may be considered as other than a point light source. The different shadows created by light coming from adjacent locations may be used to create better definition of the Shadow Tracker 6 DoF through linear interpolation of subsequent readings and pattern matching. The software may anticipate shifting shadows from the series of adjacent LSU linear segment flashes. When light from linear arrays strikes the motion tracker may read the direction of the light relative to a line of known location and orientation, which may be used to refine the 6 DoF of the motion tracker. The use of linear arrangement of LEDs allows for greater intensity of light to be delivered without creating large areas of penumbra in the cast shadows. The linear arrangement may be placed parallel with the principle axes of an associated camera. The spatial arrangement of the linear segments may serve to emphasize edge detection of shadows aligned with the linear sections. For example, top and bottom flashes may discretize the upper and lower limits of a physical object, while left and right flashes may discretize vertical edges of an object. Small penumbra effects may influence object measurements in perpendicular directions to the linear light segment in uses, but may still contain useable motion-capture data.

Figure 8A:
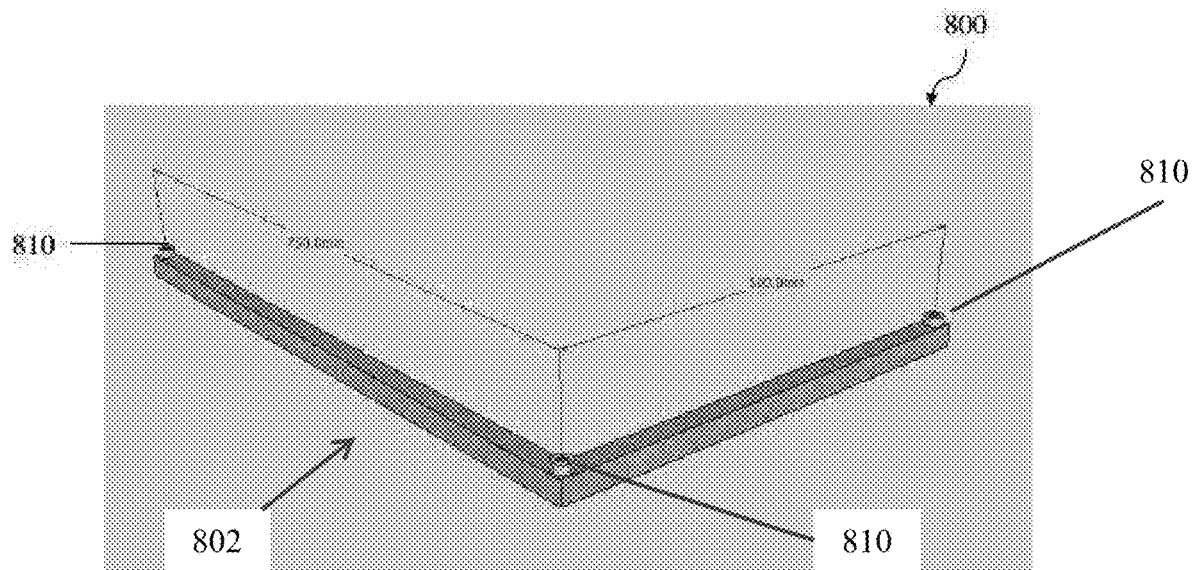
FIG. 8A is a view of an exemplary calibration frame, according to some embodiments of the present disclosure.

FIG. 8A shows an exemplary embodiment of a calibration frame 800 with 3 motion trackers 810, according to some embodiments of the present disclosure. The calibration frame may take the form of an L (L-Frame 802) with one motion tracker 810 at the vertex and one motion tracker 810 at each end point. In some embodiments, the length of the two arms may be 750 mm and 500 mm respectively.

Figure 8B:
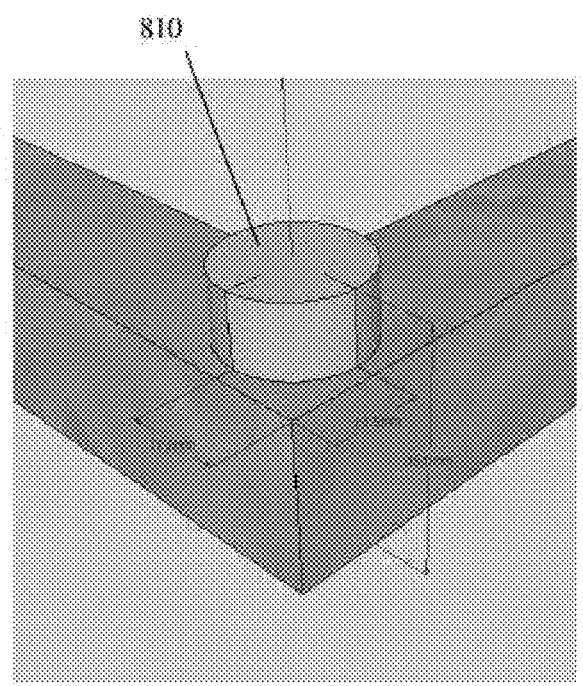
FIG. 8B is another view of an exemplary calibration, according to some embodiments of the present disclosure.

FIG. 8B is a close up view of a calibration frame corner with a motion tracker 810, according to some embodiments of the present disclosure. Data describing the intersection of 3 vectors allows for 3 paired calculations and by averaging the solutions, the 3D coordinates of each LSU impinging on the calibration frame can be determined. In calibration, three measurements may be made simultaneously of each LSU on the frame, from motion trackers labeled as Origin (at the corner of L-Frame 802), long (at the end of the long arm of the L-Frame 802), and short (at the end of the short arm of L-Frame 802). From these 3 measurements, triangulations may be constructed to locate the LSU in 3 dimensions, relative to the L-Frame 802 origin (translated to physical corner of L-Frame 802). Origin-Long, Origin-Short, Long-Short triangulations may be averaged to describe the 3D coordinate of the LSU currently illuminated. The calibration frame allows identification of the 3D location of each LSU within its range, which in turn may be linked to the sequence of each unit's on/off timing in a lighting cycle. For an LSU configured as a linear array, where each line of LEDs is a subset of the LSU, the endpoints of each linear segment may be individually mapped, and the structure of the light formation may be automatically determined in the calibration procedure.

Figure 9:
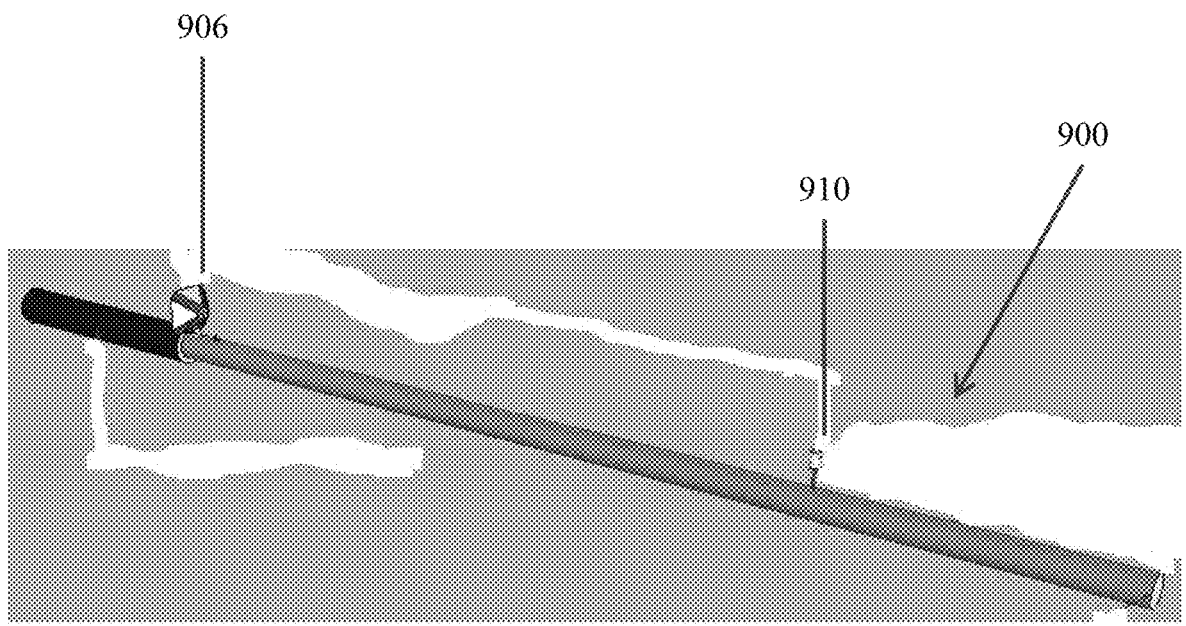
FIG. 9 is a view of an exemplary wand, according to some embodiments of the present disclosure.

FIG. 9 shows an exemplary wand 900 for calibration, according to some embodiments of the present disclosure. In addition to the calibration frame, this wand may be an adjunct tool. The wand 900 may be an elongate tool having a motion tracker 906 near one end and an LSU near the opposite end. The wand 900 may be long or short as needed for the particular application (e.g., 1 foot, 4 feet). The wand 900 may be comprised of any suitable material as known in the art (e.g., fiberglass, plastic, polyvinyl chloride (PVC)). The motion tracker 906 may be offset from the end of the wand 900 and offset from the longitudinal center of the wand 900. The LSU 910 may be offset from the end of the wand. The space between the LSU and the motion tracker may be any distance that affords reliable data (e.g., 12 inches, 25 centimeters, 100 centimeters).

The wand allows the motion-capture system operator to locate landmarks, calibrate additional light system units in the plane of the calibration frame, and to perform other functions. In some embodiments, the wand 900 may be moved into the area with the calibration frame. Once the locations of the majority of LSUs are calculated with the frame, the wand can be brought into play. The LSUs may excite the motion tracker on the wand. The motion tracker on the wand then reads the location of the LED on the wand and the calibration frame motion trackers read the wand LED. Given the data from the wand motion tracker, the wand may be used to locate other LSU in the area that are not in readable positions relative to the L-Frame 802 (e.g., on the same plane as the L-Frame, or around a corner in a complex lab set-up with doorways or furniture).

In some embodiments, the wand 900 may be pointed at important landmarks such as a knee joint, or somewhere spot in a space where a motion tracker is not located. These would be positions that should be referenced to other motion trackers in the capture process. When tracking a human body, for example, the motion tracker would typically be at the mid-point of a thigh segment and of a lower leg segment, but a researcher may need to know where the knee joint is. By referencing the knee joint with a palpation and measuring location with the wand relative to the thigh segment, calculations may be compared to the 6 DoF of one segment transformed into the coordinate system of an adjacent 6 DoF object. As such when performing landmarking operations, the object to be captured and the wand may be in the area at the same time, and the computations may be the same for locating LSUs, L-Frame, and wand. The motion trackers 700 on the object measure the coordinate system of the LSU in the area, and can indicate the location of the wand LSU 910 relative to the wand tip 902. The system LSUs may excite the motion tracker 906 on the wand 900, and, given the resultant 6 DoF information about the motion tracker, the 6 DoF information about the wand tip can be interpolated. The LSU on the wand may flash serially with those LSUs in the area such that a special wand-LSU timing may be incorporated into the LSU activation pattern as controlled by the computer system. The computer system "knows" that the wand-LED is a non-stationary light source. The motion tracker of the wand, the L-Frame 802 and the object to be tracked can be computed based on the wand-LED location relative to the 6 DoF of each motion tracker in line of sight to the wand-LED.

Another use of the wand 900 may be to point the wand 900 directly at an LSU to determine the direction that each LSU may be pointing at that moment in time. If the wand is generally perpendicular to the LSU, this added information (besides the 3D coordinates of the LSU) consists of the direction from which the light of each LSU may be coming into the area. Since the LSU has two sides, one where the light comes out, and one mounting side (mounted to a wall, a ceiling, a floor, an object, etc.), the light emitted by the LSU may only be projected from roughly a 180-200 degree portion of a sphere. Giving the system software the center point and orientation of the LSU, and thus the spherical portion of light, may assist in reducing the complexity of computations.

Figure 10:
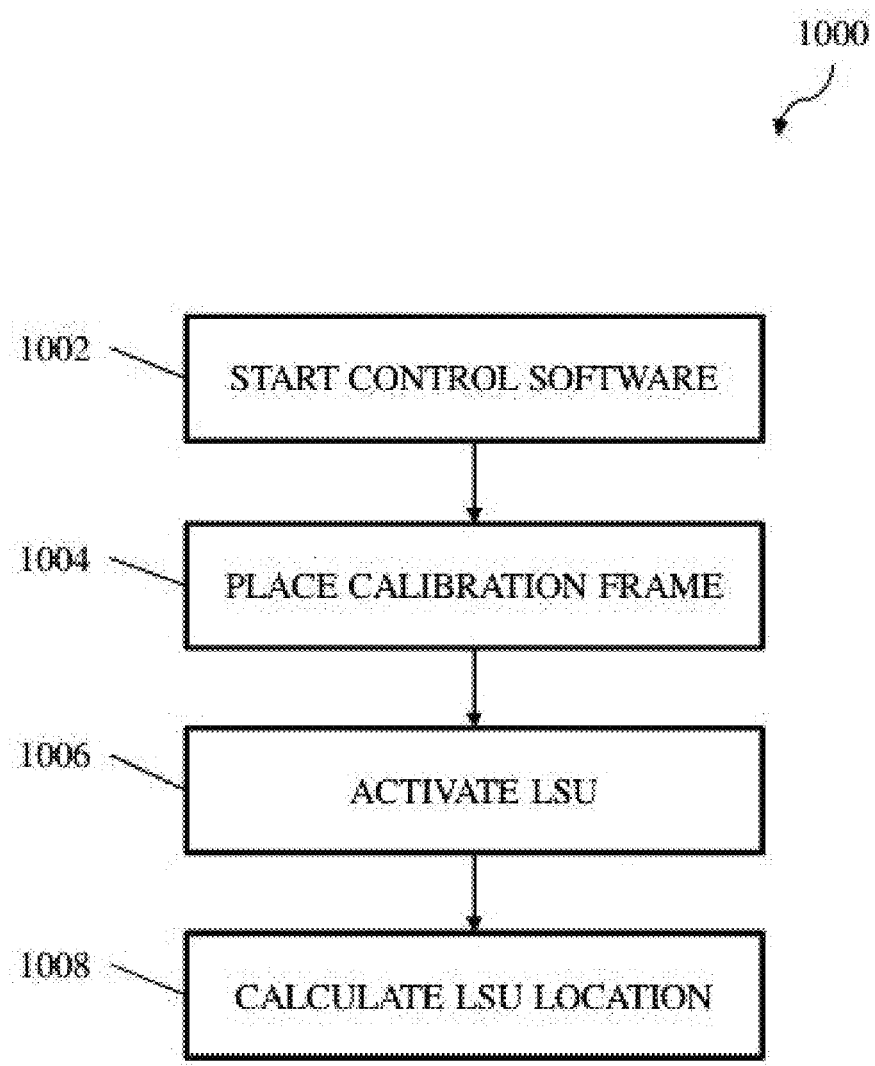
FIG. 10 is a flow diagram illustrating an exemplary calibration method, according to some embodiments of the present disclosure.

FIG. 10 is a flowchart showing an exemplary calibration method 1000 for a camera-less motion detection system, according to some embodiments of the present disclosure, as shown generally in FIG. 2. At step 1002, a proprietary software (e.g., system software) may be started on a computer system, the computer system may turn on all LSUs. Each LSU may illuminate in a sequence, repeating on/off cycle with 2 ms on times. The system software may detect (via radio, Wi-Fi, or Bluetooth transmission of data) for the presence of motion trackers in the vicinity.

At step 1004, the calibration frame may be placed at a desired location and orientation, aligning the desired origin with the corner of the frame, and the long and short arms pointing in desired X and Y directions. This location of the L-shaped frame sets the Global Coordinate System (GCS) of the volume or area. When the calibration frame is placed in a position such that both arms are horizontal, by default, the origin of the GCS (0,0,0) is at the physical corner of the L-Frame, the short arm of the frame describes the x-axis (usually to the right), the long arm describes the y-axis (usually anterior to the person holding the L-Frame 802), and the z-axis would then be, by definition, pointing upward (away from the transverse plane of the frame or ground). The origin may be further translated mathematically from the corner of L-Frame 802 to any location in the volume or area, and the long and short arms may be designated as any coordinate direction, and the coordinate system may be tilted in any of three directions relative to the L-Frame 802 as well.

In one embodiment, the L-Frame 802 has 3 motion trackers on it, one near the junction of the short and long arms and called "Origin," and one near the end of each arm, called "Long" and "Short." The motion trackers may be attached to the L-Frame 802 with the local coordinate system of the motion trackers aligned with the arms of the L-Frame. The L-Frame 802 may provide a consistent way to align the Global Coordinate System of the volume or area in the system software with other structures in the space. These structures may include an instrumented force plate, a treadmill, stairs or other any other structure or feature. Conveniently, the two arms of the L-Frame 802 ensure that the calibration device lays parallel to the transverse plane of the floor. Other smaller calibration frames may be fabricated with discrete spacing between motion trackers to allow for smaller or larger measurement volumes, and or for measurement volumes with local coordinate system origins not aligned with the transverse plane of the ground. Calibration frames may be in the shape of a right triangle or any other shape that allows calibration of the system.

At step 1006 of the method embodiment depicted in FIG. 10, the LSU to be calibrated may be turned on and off with a 20 microsecond interval. The system then records and transmits (via RF, WiFi or any other transmission method) one 2-dimensional (2D) angle from each of the three exemplary motion trackers on the calibration frame to the system software on the computer system. With three 2D angles between the calibration frame and the first LSU, and known physical separation between the motion trackers on the rigid L-Frame, a geometric triangulation process may compute the 3 dimensional coordinates of the first LSU. At step 1008, the location of the LSU may be calculated based on the transmitted readings. Two motion trackers on the L-Frame 802 may be sufficient for computation of the LSU locations, yet three motion trackers allow for redundancy and error checking (i.e., Origin-Long, Origin-Short, and Long-Short). The coordinates of the LSU may be calculated in a global coordinate system relative to the corner of the L-Frame 802 with directions parallel to the long and short calibration frame arms. In this manner, the 3D coordinates of every LSU in the volume may be stored in the system software and referenced each time the software commands the corresponding LSU to illuminate.

With the system software, the newly computed LSU location may be rendered as a green icon in a wireframe representation of the motion-capture volume in 3D. As each LSU is located and calculated, it too may be placed in the 3D preview. The L-Frame 802 and its motion trackers may also be shown in the 3D preview.

In some embodiments, for LSUs that are located on the floor or in other locations where it may be difficult to obtain a line of sight between the LSU and the motion trackers on the L-Frame, a secondary portion of an exemplary calibration process may be invoked. An LSU with sub-threshold location accuracy, as determined by preset values in the system software, may be displayed in red in the 3D preview, near the best-approximation location. If no 3D location approximation is possible, the non-located LSU may be displayed in a list of items, in a side panel adjacent to the 3D view.

Such secondary calibration may continue from the standard calibration with each LSU still flashing in the same 20 microsecond on/off preset sequence. The operator may pick up the L-Frame 802 and point the side of the L-Frame 802 with the motion trackers toward the unresolved LSU. The operator may hold the L-Frame, in a relatively motionless position, to present the motion trackers to the missing LSU until enough light system cycles occur to reliably compute the 3D coordinates of the missing LSU. The system software, utilizing the data from LSUs with known 3D coordinates, may track the 6 DoF of the L-Frame 802 as it is moved. Then the coordinates of the unknown LSUs may be computed, via the intermediate transformation of coordinates from the 6 DoF information of the L-Fame relative to the GCS origin set in the first calibration step. The 3D preview may change the color representing each LSU to indicate to the operator whether each LSU has been successfully located or not. The operator may check in the system software that all LSU coordinates have been computed. The system software may clearly indicate which if any LSU do not have coordinate data and prompt the operator to rectify that situation, by bringing the L-Frame 802 back into the volume such that the system software may extract more data on the missing or weak motion tracker coordinate data.

Figure 11:
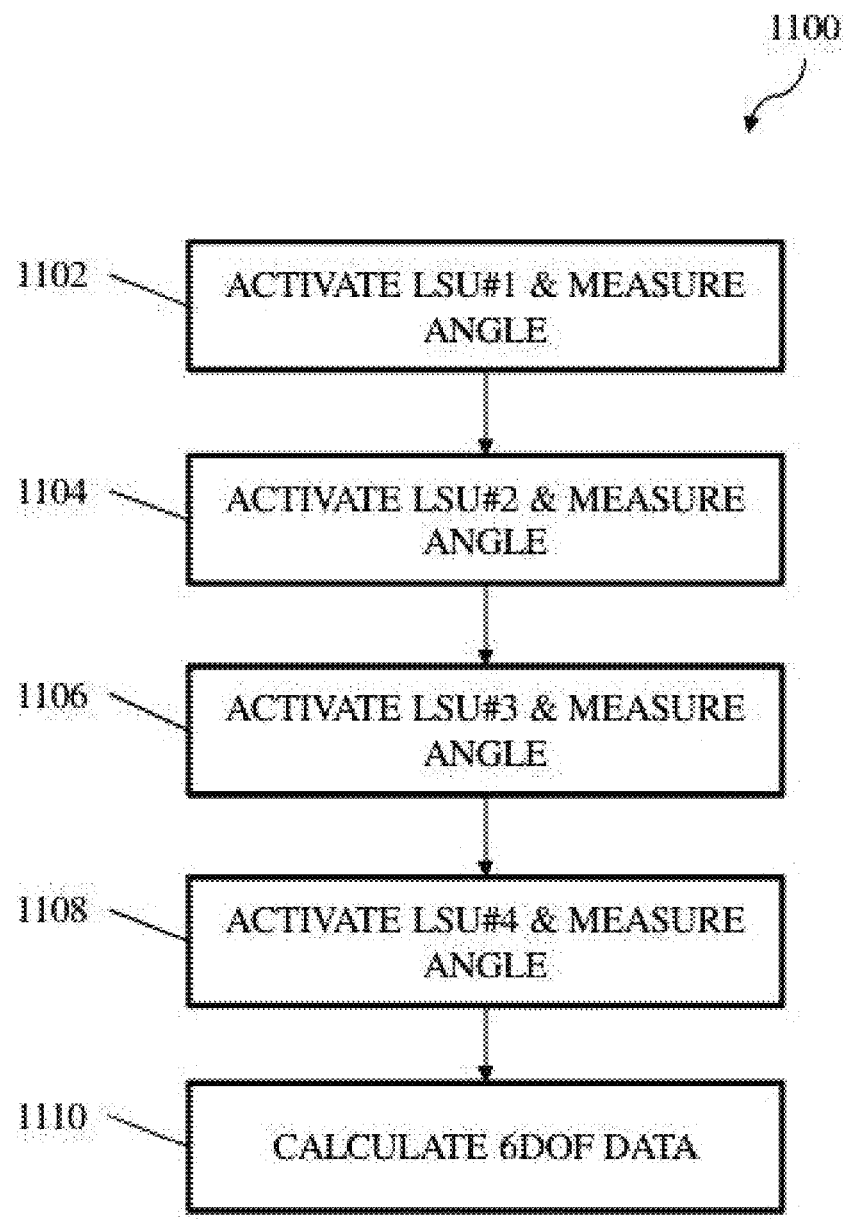
FIG. 11 is a flow diagram illustrating an exemplary method of motion capture, according to some embodiments of the present disclosure.

FIG. 11 is a flowchart showing a method of motion capture 1100, according to some embodiments of the present disclosure. At step 1102, a first LSU may be activated and a motion tracker may transmit data that allows calculation of the 2D angle in the local coordinate system (LCS) of the motion tracker to the known coordinate location of the LSU #1. This yields the two angles between the motion tracker and the LSU. The distance between LSU #1 and the motion tracker may not be required, although light intensity could approximate the distance between motion tracker and LSU #1, if the power of LSU #1 is known. If the exact direction of LSU #1 to the motion tracker is unknown, and it could be anywhere on a sphere surrounding the LSU, no GCS coordinates or rotations of motion tracker may be determined without additional input.

At step 1104, a second LSU may be activated and the motion tracker may transmit data that allows calculation of the 2D angle between the LSU and the motion tracker in the LCS of the motion tracker to the known coordinate location of LSU #2. Thus, in a triangle among LSU #1, LSU #2, and the motion tracker, one side and one angle may be known. The distance of the motion tracker from the line between LSU #1 and LSU #2 may be calculated via triangulation between the three objects. The motion tracker may be anywhere on a circle of known radius perpendicular to the line between LSU #1 and LSU #2.

At step 1106, a third LSU may be activated and the motion tracker may transmit data that allows calculation of the 2D angle between the LSU and the motion tracker in the LCS of the motion tracker to the known coordinate location of LSU #3. This third observation may allow a second triangle construction (LSU #2-LSU #3-motion tracker). A coordinate system transformation may be performed from LCS of the motion tracker into GCS of lab and LSUs #1, #2 and #3. The intersection of 2 circular equations, so determined, may result in two 3D coordinate locations, and the intersection closest to the origin of the GCS may be selected. The angles of motion tracker may be taken from the three pairs of angles read during previous measurements. 6 DoF of the motion tracker may be set.

At step 1108, a fourth LSU may be activated and the motion tracker may transmit data that allows calculation of the 2D angle between the LSU and the motion tracker in the LCS of the motion tracker to the known coordinate location of LSU #4. This fourth observation may allow LSU #3-LSU #4-motion tracker triangle computation. Since 2 circular intersections occur, the solution closest in 3D space to the prior motion tracker location may be selected. The 6 DoF data may be updated.

At step 1110, after the four measurements and calculations, the final 6DOF data of the motion tracker may be calculated.

During active collections of motion-capture data, the computer system may combine the time at which each LSU turns on and the location where the LSU is located in 3D space, as well as how the LSUs are oriented. By this combination of time, space, and layout, each motion tracker may indicate its current orientation relative to each LSU in series, and, by the time a motion tracker unit makes 4 measurements, its 6 DoF data may be realized. In some embodiments, the motion tracker may only measure 200 degrees of angular excitation, and there may be instances where the 3 measurements required to determine the 6 DoF may be not in sequence. Thus, interpolation may be introduced to correct for excitations of a motion tracker due to occlusion or other failures to obtain line of sight between a motion tracker and the lighting system unit at a particular instant. The computation, even with 3 sequential measurements, may be based on a serial computation where linear predictive estimates may be employed. Thus, once an initial computation of 6 DoF data is made, no accelerations greater than 1000 meters per second squared may be accepted, and no large shifts in displacement or orientation may be accepted. Also, the last location, current location and predicted future location of the motion tracker may be known.

The LSUs may turn on and off at microsecond intervals, with no delay between pulses. The LSU may operate in a seek/standby mode where the location and the number of clusters in its configuration may be transmitted for each LED. Whichever cluster may be recognized initially becomes the first LED of its local group of clusters to be illuminated. As other LED clusters in the group get recognized, the cycle of cluster on/off pattern increase speed such that each recognized cluster signature may be added to the list of known 3D coordinate points that each particular recognized cluster has shared. Each new LED cluster may cease to flash it's coordinates or ID, and simply turns on and off at a prescribed time interval following the master LED up to a number divisible by the total number of clusters in the group. Once 4 lights have been recognized and added to the light sequence, the 6 DoF of a sensor may begin to be computed uniquely. The light system may operate in this mode preliminarily, to initialize the 6 DoF of each motion tracker in the volume. As the 6 DoF of each motion tracker is determined, the system may select a standard operating mode.

A metaphor of how the system operates may be the tightening of lug nuts. In a five bolt pattern, a first bolt may be tightened, then its most opposite may be tightened, then across to the third bolt most opposite to both the first and second, then the fourth and finally the fifth. This forms a 2D pattern. Using this metaphor as a method for the sequence of 3D light flashing, the first five lights to flash in such a system may be a base light near a computer system, then the light most distal from that base light in 3D space, then a point distal to both the first and second light point, and so on. The maximal distance from light source to light source may cycle until all lights in the system have lit once. This initial cycle of flashing light units may allow a low frequency cataloging of the 6 DoF information for each motion tracker in the light saturation area, thus allowing for a specialized LSU flashing pattern designed to capture as many motion trackers at the highest sampling frequency possible. This scheme of light flashing may then be optimized to create the widest dispersion of lights illuminating in sequence surrounding the greatest number of motion trackers. As such the largest number of motion trackers oriented with their light sensitivity aperture or arcs facing a group of light units may allow the greatest number of light readings by the greatest number of motion trackers, with the largest apparent separation between light units, as the greater the apparent separation, the more robust the computation of each triangulated location of a motion tracker may become.

In this embodiment, once the cycle of all lights is passed, and 6 DoF is computed for each motion tracker, the pattern of flashing may change. This change from all lights flashing in series to subsets of lights flashing in series may allow an increase in the sampling frequency of each motion tracker if desired. By considering the motion trackers in FIGS. 8 and 9 with a 200 degree hemispherical detection angle and the 6 DoF of each, the system may compute the light sources at the location most visible by all motion trackers. These lights may flash preferentially.

Second, in one embodiment, to best track a single motion tracker five lights within the 200 degree visibility cone of a specific motion tracker may light in as close a timeframe as possible. These 5 lights may be selected to maximize the apparent angle between the motion tracker and the light. It may look like the 2D image attached above. In this way the five light activations detected by the motion tracker occur near in time and at the greatest angular departure from the light source neighbors.

Third, in one exemplary embodiment, a set of non-common lights may be programmed to flash simultaneously, such that two (or more) data points may be acquired at the same instant in two (or more) separate groups of motion trackers. This may be visualized as a person wearing a suit covered with motion trackers, and the lights on the left may potentially be flashed at the same time as lights on the right side of the body, as the motion trackers on the left may be occluded by the body (and the physical limits of angular sensitivity—200 degrees) such that lights on the opposite side of the room may be not detected, and may serve to excite other groups of motion trackers chips facing that general direction. Furthermore, individual motion trackers may measure these non-common LSU lights simultaneously if the orientation and position of each motion tracker allows. Since a motion tracker may have 4 (or more) discrete light direction detecting chips built into it, intentionally selecting LSUs in the system to flash that strike different chips on the motion tracker (likely on orthogonal or opposite walls of an LSU setup) enable a motion tracker to take readings from two, three, or more LSUs simultaneously. This may allow a parallel mode of data capture to be taken preferentially over serial data interpolated to a master frame rate. Non-common LSU operation may begin after each motion tracker has an established 6 DoF initialized and may be controlled by the system software.

In some embodiments, two or more motion trackers may be affixed to a single rigid platform such that the known layout geometry of the motion trackers may facilitate extraction of the platform's 6 DoF, including velocity and direction of the platform from fewer than 4 light signals. This may be similar conceptually to the calibration frame, yet the platform may be fabricated small enough to allow unimpeded movement dynamics of the object the platform is attached to, for the purposes of motion capture.

In some embodiments, motion trackers may be always on and actively measuring light strike angle. Once a motion tracker detects two 20 microsecond light pulses from two different directions (incoming angles) within 1 second, the second pulse may be measured and the data may be broadcast via RF with a "Hello, serial number xxx motion tracker may be here" signature. Each subsequent 2D angle measure may be transmitted along with serial number of the motion tracker sending it.

The motion tracker trajectory in 6 DoF may be conditional, and checked for plausibility, by limiting the moment-to-moment 3D displacements and 3D rotations to lower than user selected maximums. The motion tracker for instance may not be allowed to rotate 180 degrees, or translate 1 meter between two measurements less than 10 ms apart.

In some embodiments of the system, the LSU, motion tracker and the system software may be serial. This means only one reading between motion tracker and LSU may be made at a time, and motion of the motion tracker occurring between one discrete measurement at one LSU and the next measurement at a nearby LSU may induce error into the 6 DoF solution. Subsequent readings by the motion tracker at each LSU recorded as part of the capture process may have the option to be linearly interpolated in order to approximate a synchronous recording. These measurements may then be brought to a master collection frequency with a single frame rate similar to other types of motion capture. The linear interpolation of direction toward each LSU may be performed on the two angles recorded from the motion tracker recording data.

In some embodiments, system software is provided to collect the motion tracker data and assign each 2D measurement to a particular LSU. The system software may then perform linear interpolation on the two angle data sets at each LSU, at user-defined limits. The limits on interpolation may define a default set to fill data gaps of no greater than 1 second (to be determined). The primary use of interpolated data may be to bring the computation of the 6 DoF of a motion tracker to a master frame interval. The second function of interpolated data may be to add error checking to the 6 DoF motion tracker data, by creating additional triangulated solutions from data points missing from an LSU that was seen by the motion tracker, was occluded from the motion tracker, and reappeared to the motion tracker.

System software may respond and start recording 2D angle information from each subsequent 20 ms LSU pulse. After three successful 2D angle measurements paired with 3 LSU locations, an initial 6 DoF motion tracker solution may be output. Based on the vector direction perpendicular to the 6DOF plane of the motion tracker, and an angular detection range of 110 degrees (+/−55 degrees in four cardinal directions from this vector), a map of LSUs visible to the motion tracker may be created. The LSU locations within this cone of visibility to the motion tracker may be then flashed referentially, along with a set of LSU locations slightly beyond this scope, as the motion of the motion tracker may bring the LSU outside the initial cone inside a new cone in the subsequent frames. With 4 chip motion trackers, the cone of visibility may be increased to 200 degrees, with a central area of 20 degrees that may be read by both light-direction detector 702 pairs. These ranges increase with the more complex 8 light-direction detector 702 motion tracker of alternative embodiments. After two determinations of the 6 DoF of the motion tracker, a prediction envelope may be created. The prediction envelope may take what the 6 DoF was in previous measurement, what it currently is, and with a linear extrapolation predicts where it may be on the next measurement. Thus the LSU locations ahead of where the motion tracker may be pointing may again be given preference to pulse next, just as the LSU locations trailing where the motion tracker was facing may be de-prioritized.

In some embodiments, the system may have LSUs placed on all 4 walls, ceiling and floor. In some embodiments, the system may only have LSUs on one wall or part of a wall only. In some embodiments, a retail store may wish to have interactive single wall displays for augmented reality reflections of a window shopper to appear in their brand's apparel. Thus, the single wall or portion of a wall may house the lighting system. The sensing system may use multiple points of reference all situated in a single 2D wall or window surface. The motion trackers facing away from the wall may not pick up these light flashes, but enough motion trackers on the anterior of a person's body may be excited by the lighting system and create a mathematical description of the anterior facade of a person's body (in the window shopper example), with enough detail to allow the appropriate rendering of the augmented reality aspects onto a motive reflection of a person in real time. For example, the motion tracker may be temporarily affixed to skin or clothing or woven into the fabric (embedded) in clothing. This may give retailers a way to measure your body size and make custom fitted clothing for instance.

In some embodiments, a lighting system may be installed to a machine, such as an automobile, so that another vehicle equipped with motion trackers may measure the approach and proximity of the car with the lighting system for warning the driver or as an information source for an autonomous driving system. In some embodiments, watercraft and aircraft may have docking or landing facilities equipped with the lighting system, and ships, airplanes and helicopters may have a single or multiple motion trackers to sense their position and orientation relative to the LSUs, again as a collision warning system, or for future autonomous navigation and docking systems. Lighthouses along shipping routes may be information sources for the motion tracker based motion-capture system. In these scenarios, individual lights at a distance may appear as a single light source, and a motion tracker motion-capture system may detect orientation relative to that single light source (appear as a single light albeit flashing as individual lights). As a vehicle (land, air or sea), approaches the facility or another vehicle with a lighting system and the individual light sources may be discriminated from one another (placed to maximize inter-light source distance), the full 6 DoF data of the motion tracker thus relates the orientation of the vehicle with the motion tracker system to the position and orientation of each and every other vehicle (or object) equipped with the lighting system.

In some embodiments, the lighting system may be incorporated into a television display. A liquid-crystal display (LCD), or individual pixels formed in other technologies, may flash with a signature pattern to identify its position to a pair of eyeglasses or other head mounted device equipped with the motion tracker motion-capture system. The lighting of pixels in the display (e.g., near each of the four corners of a rectangular display) may allow calculation of the viewer's position and orientation relative to the viewing medium (screen) with 6 DoF. With this information, 3D display elements may be inserted into the video content on the screen being viewed to allow a 3D view of the image and perhaps virtual reality interaction. In addition to adaptive, external LCD screens, transmitting the 6 DoF of the motion of each eyeglass lens surface of a wearer to a projector system, left and right video images may be directly painted on the lenses thus creating a 3D video effect. (The Texas Instruments digital micro-mirror device (DMD) may be one such technology.) With a wall mounted DMD, images may be presented to the eyewear of multiple wearers simultaneously with motion tracker lenses having 6 DoFs. Alternatively, for users wearing the motion tracker eyeglasses, a smartphone could be built with a DMD instead of a screen.

Figure 12A:
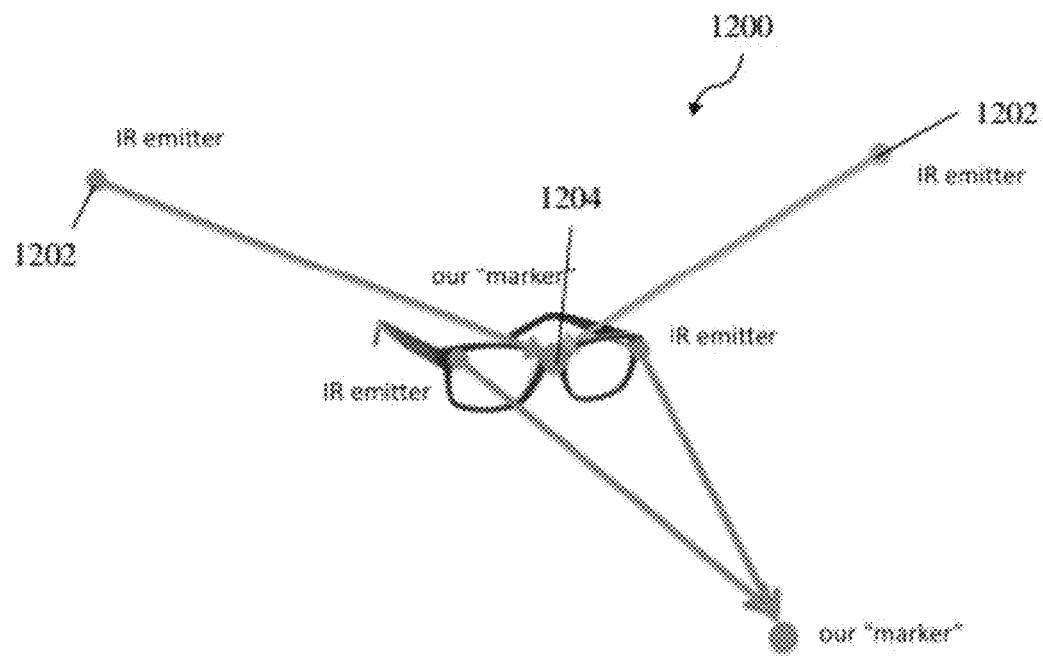
FIG. 12A is a view of an exemplary motion tracker mounted on an eyeglass frame, according to some embodiments of the present disclosure.

FIG. 12A shows an exemplary motion-capture system 1200 with a motion tracker mounted on an eyeglass frame, according to some embodiments of the present disclosure. In some embodiments, a small lighting system (up to 10 individual lights) 1202 and a motion tracker 1204 with LEDs may be attached to an eyeglasses frame. With the ability to receive and transmit 6 DoF of each eyeglass lens relative to each of the wearer's eyes, augmented reality systems may project correct stereoscopic imagery onto the lenses for the wearer. Furthermore the 6 DoF of the eyeglass frame mounted lights may then be used as a system-within-a-system to enhance finger tracking. The flashing of LSU LEDs on an eyeglass frame may be patterned in timing and spatial layout (arrangement of LSUs on the frame) to provide a signature ID to authenticate users or provide password access to software, and devices (smart phones or door locks as examples). Similarly, the ID flash of a wearer's eyeglasses may selectively allow or block advertisers from presenting content, based on the wearer's opting into promotions etc. As IR light overwhelms video capture, the flashing of LSU on eyewear may be patterned to serve as a privacy screen from unauthorized cameras and may be synchronized to allow authorized image capture.

Figure 12B:
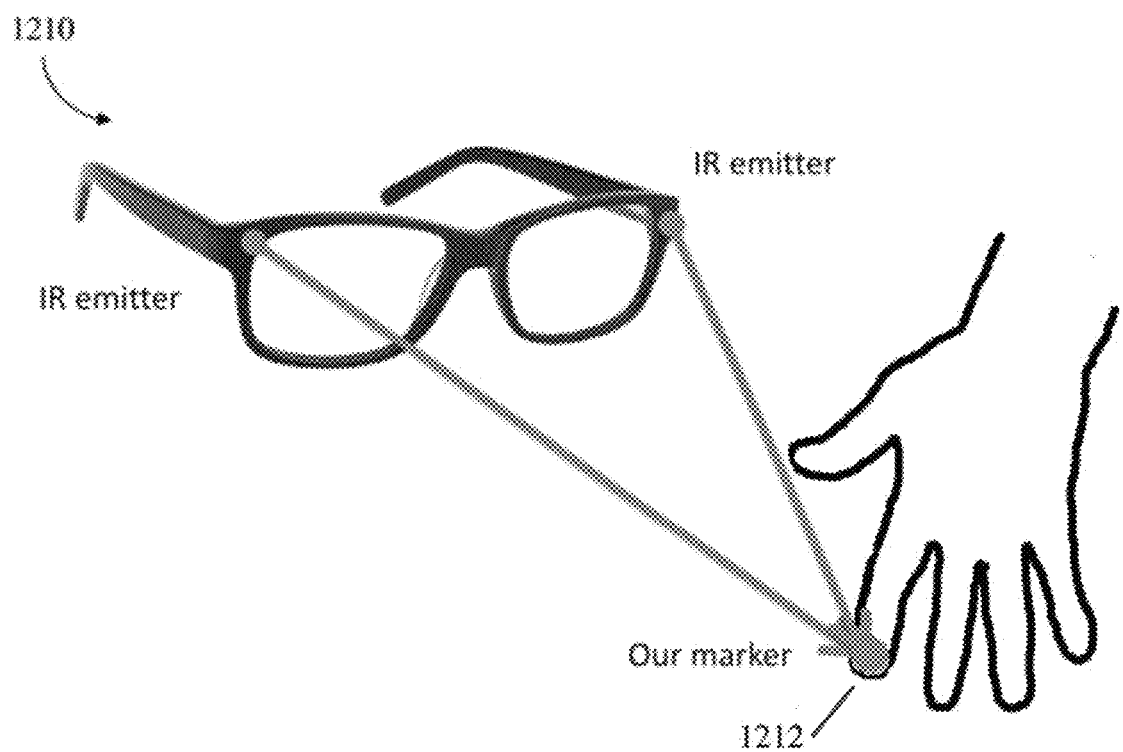
FIG. 12B is a view of an exemplary motion tracker mounted on a human fingernail, according to some embodiments of the present disclosure.

FIG. 12B shows an exemplary motion-capture system 1210, according to some embodiments of the present disclosure. In some embodiments, the motion tracker/LED unit 1212 may be glued to each fingernail. The finger (and toe) nail devices with motion tracker/LED and bending/vibration of the nail bed operate as a response to 6 DoF configurations and motions of the fingertips, but also may operate on a programmable schedule to vibrate or provide bending specific types of signals to the wearer. One type signal would be an alarm, or alert to wake the user in the morning, with a gentle pulsating of the fingertips. By alternating which finger vibrates or bends, specific information may be ingrained in the pattern of alerts, such as the identity of a caller, or from whom an email or text message has arrived. These signals may be repeating patterns of stimuli. These signals may serve as general notifications or reminders from a wearer's calendar, email, web search results, phone calls, and likes, but also the vibrations may and may be patterned to illicit physiological effects, including but not limited to scalp hair re-growth. In some embodiments, by creating a cascade of vibrations and bending moments on each fingernail in sequence or simultaneously, the effect of a nail rubbing (or "balayam") practice may be delivered without the need to remember to perform the practice, or to perform the practice manually at all. Furthermore, to enhance the sense of touch, stochastic resonance vibration patterns may be embedded at sub or supra sensation thresholds, which have been shown to improve lower the tactile sensitivity threshold and when applied to the feet, the elderly show reduced postural sway. In some embodiments, the haptic fingernail may perform the function of touch without touching.

In some embodiments, the lighting system may have the shape of an arch or arbor, with a constant or non-constant radius, shaped to fit the needs of the application. This setup may allow a mobile lighting system to be placed over and above a piano keyboard, for example, so motions of a performer's hands may be captured when motion trackers are affixed on each finger segment (or simply on each fingernail) while they play the piano. In some embodiments, an arbor of lights (or a pair of arbors) may be placed facing the frets on the neck of a guitar, and motion trackers may be placed on the body for study of a performer. In some embodiments, a similar arbor of lights may be used for other instruments such as clarinet, oboe, saxophone, trumpet or violin.

For use in reality-based animation, the sensing system may have a small form factor such that it may be applied to an actor's body and face, to give an animator much more exact data, namely the rolling, pitching and twisting of the skin's surface during the unique expressions of a character, which exist beyond the simplistic 3D positional data. The sensing system may narrow the uncanny valley and bring hyper-realistic animations greater believability and a more natural appearance. This ability may be unattainable with 3 DoF systems, and also serves to greatly simplify the process of tracking the major segments of the body in 6 DoF as a single sensor may be attached to the midpoint of a segment instead of a triad or group of four as historically practiced.

Capturing the curl of the lip may be easy to accomplish with a few motion trackers strategically attached. When the shadow across each pair of light-direction detectors 702 may be read, cast by at least 3 individual light sources, it extracts both 3D position and the 3 angular descriptions of that a single point, thus the user gets twice the information from one discrete location. Importantly, the motion tracker may function as part of a stand-alone system as it does not need to be hybridized with inertial motion sensors or other separate systems, which often yield inconsistent results.

The lighting system units may be added to improve the function of an existing motion-capture systems, such as those produced by SiMi® Reality Capture Systems GmBh. The SiMi® system has ring lights but they may be primarily used during their calibration procedure and not during collections. One SiMi® product called Shape uses the camera system to capture the silhouette of a human actor inside the field of view, by background subtraction. The SiMi® Shape system uses 8 cameras, and the data output may be a result in combining these 8 silhouettes. By alternatively flashing the LED rings on each of the 8 SiMi® system cameras, and by flashing LSU added to the periphery of the volume, shadows that may be cast may be collected as part of the standard video frames of the measurement. Each of these cast shadows may be the projected result of the light interacting with the human in the volume. The silhouette tracked model built by SiMi® Shape may be likewise be projected onto the walls and floor of the volume, determined by the point light sources of the SiMi® camera LED rings and LSU. To utilize this added data, the flat surfaces in the lab must be mapped during the calibration process (walls, floor, ceiling, furniture, etc.), and measurements of light absorption added. Non-absorptive or transmissible or reflective surfaces or irregularly textured surfaces may not create an adequately defined shadow. Some cameras may not be positioned to see both the human actor and the cast shadow from other light sources. Thus a comparison between actual shadows on the walls and floor in the video file may be made with the shadow projection from the 3D SiMi® Shape model. Bringing in extra LSUs effectively increases the number of shadow silhouettes while keeping the SiMi® Shape system at 8 cameras. Furthermore, the 2D appearance of the shadow cast by the LSU or the SiMi® camera LED ring may be native to the LCD chip used to capture the video images, and a direct transformation may be made from shadow projection to image. The LSUs may be placed into the SiMi® system at locations that cast the shadows containing the most information for given human postures and activities, locations that may not be ideal for camera placement.

Figure 13A:
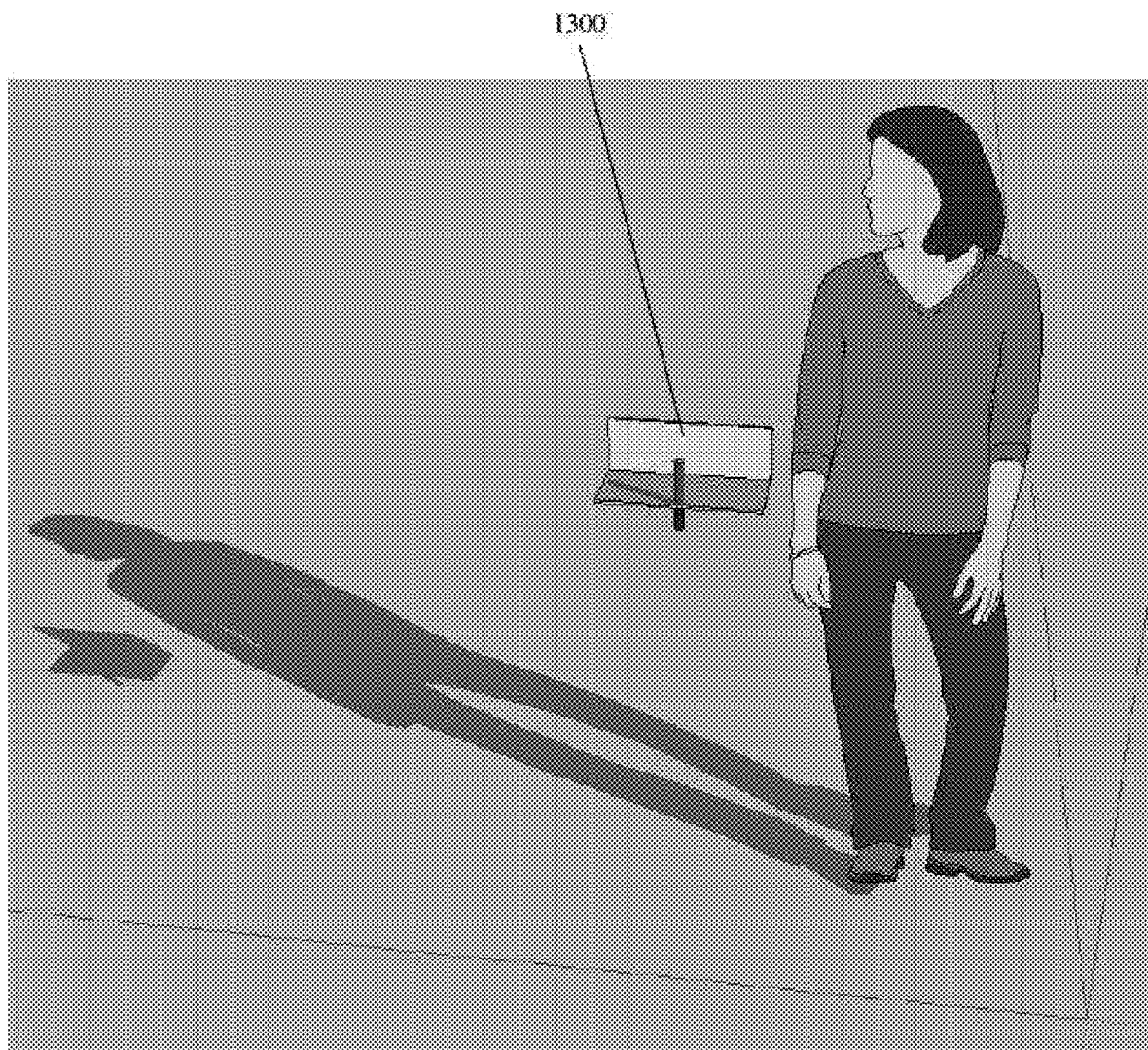
FIG. 13A is a view of an exemplary calibration tool, according to some embodiments of the present disclosure.

FIG. 13A shows a calibration tool 1300, according to some embodiments of the present disclosure. The shadow box calibration tool 1300 may allow the verification of light source location (both LSUs and SiMi® LED rings), and consists of a cylinder on a handle, and a two-sided box with a floor and one wall at 90 degrees. This device allows measurement of the shadow cast by the light source with the known geometry of the box casting the shadow and the dimensions of the surfaces that the shadow is projected upon. From these measurements, the 3D location of the light source may be computed, and then utilized in subsequent SiMi® Shape recordings of a human actor.

The hybridizing of the SiMi® Shape system with LSUs and motion trackers, the SiMi® silhouette tracking, the projected shadow tracking, and the body surface tracking may all happen concurrently and in a manner that serves to reinforce the quality of the whole-body, motion-capture output.

Figure 13B:
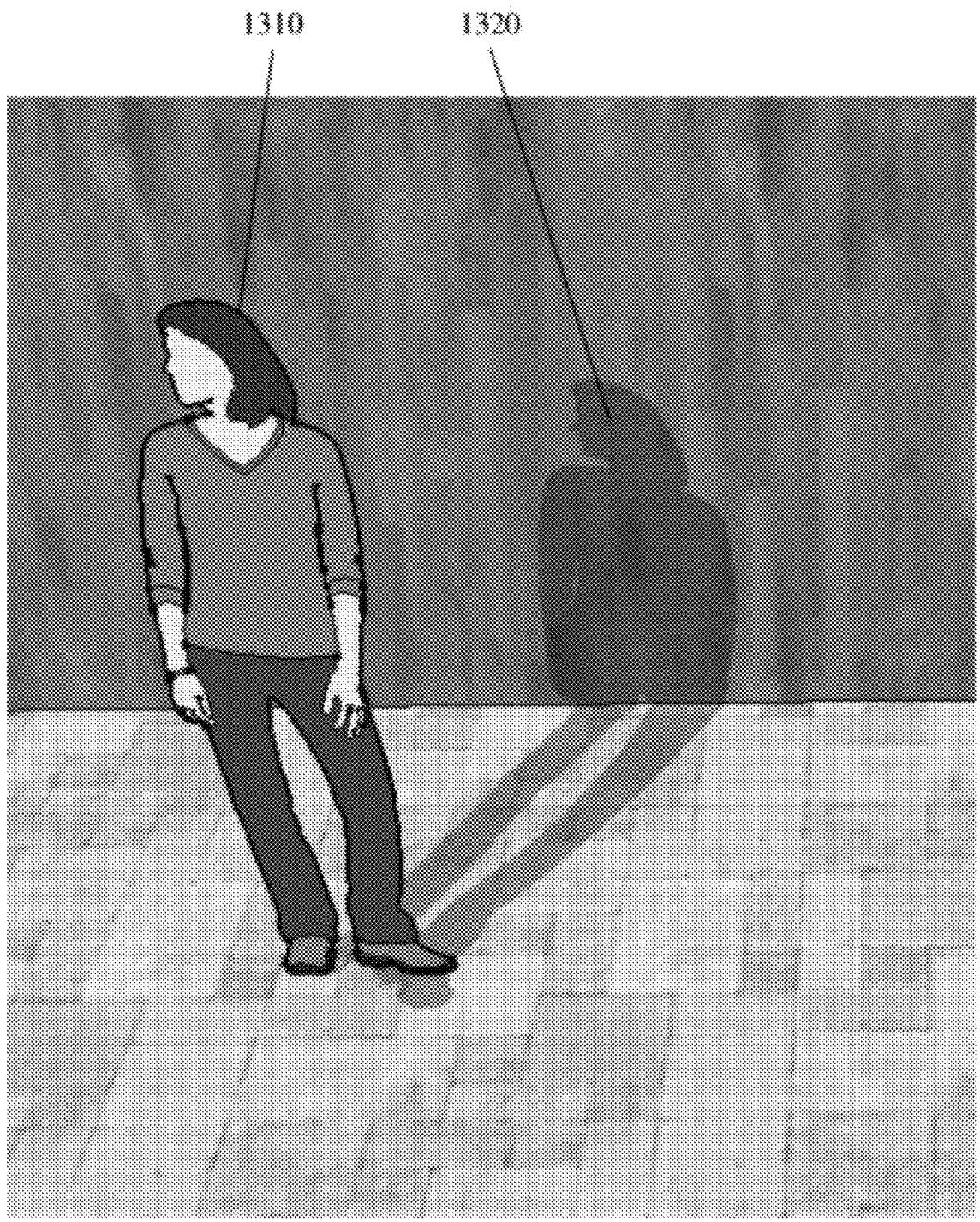
FIG. 13B is a view of an exemplary silhouette effect, according to some embodiments of the present disclosure.

FIG. 13B shows an exemplary silhouette effect, according to some embodiments of the present disclosure. The light source creates a shadow based on the curved surfaces of the human body 1310, and the shadows 1320 are cast on the wall. These shadows may be transformed back to silhouettes at the actor's location and may contain segmentation not apparent in the direct view of the subject (i.e. arm/torso). The curvature of human limb segments may be thus added information beyond the intersection of silhouettes that rely on assumptions of roughly cylindrical segments.

The benefit of hybridizing the motion tracker with onboard LEDs, and a camera-based motion-capture system such as SiMi® Motion may be that with the motion tracker LED active and being tracked in 3D by 3 or more cameras, a single light direction measurement may be sufficient to determine the 6 DoF of the motion tracker, thus enabling 6 DoF data capture in a parallel mode at the master frame interval, and avoiding the interpolation errors that may occur during stand-alone serial capture of motion tracker data. The downside may be as always, cost of the camera-based system.

The present disclosure may be not to be limited in scope by the specific embodiments described herein. Indeed, other various embodiments of and modifications to the present disclosure, in addition to those described herein, may be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art may recognize that its usefulness may be not limited thereto and that the present disclosure may be beneficially implemented in any number of environments for any number of purposes.

The invention claimed is:

1. A method for tracking motion comprising:
detecting, at two optically isolated points of a motion tracker device, intensity of a light from a light array comprising a plurality of light sources configured to illuminate in sequence, wherein the optically isolated points are disposed at a distance from one another such that a variation in intensity of light due to shadowing effects from the plurality of light sources is different at the optically isolated points;
generating, by the motion tracker device, a current signal representing a photodiode differential between the two optically isolated points and proportional to the intensity of the light; and
transmitting, by the motion tracker device, the current signal to a computing device.

2. The method of claim 1, wherein the motion tracker device comprises a substrate and at least a first light-direction detector and a second light-direction detector mounted on the substrate at different locations such that an angle of incidence of light from the light array is different on the first and second light-direction detectors.

3. The method of claim 1, further comprising determining, by the computing device, the motion of the motion tracker device with six degrees of freedom based on the current signals transmitted from the first and second light-direction detectors.

4. The method of claim 1, further comprising emitting, by a light emission source of the motion tracker device, a second light.

5. The method of claim 4, wherein the light emission source is a light-emitting diode (LED).

6. The method of claim 4, wherein the light emission source comprises a second light array comprising a plurality of second light sources.

7. The method of claim 6, wherein the emitting comprises illuminating the plurality of second light sources in sequence.

8. The method of claim 1, further comprising mounting the motion tracker device on a human fingernail.

9. The method of claim 1, wherein the plurality of light sources comprises a plurality of light-emitting diodes (LEDs).

10. The method of claim 1, further comprising illuminating the plurality of light sources in the sequence.

11. The method of claim 10, wherein the plurality of light sources is arranged in a linear arrangement or a rectilinear arrangement and illuminating the plurality of light sources in the sequence comprises individually flashing each of the plurality of light sources sequentially along the linear arrangement or the rectilinear arrangement.

12. The method of claim 1, wherein the plurality of light sources is arranged relative to the substrate such that light output from the plurality of light sources is estimated as a point light source at the motion tracker device.

13. The method of claim 1, further comprising:
  detecting, at two additional optically isolated points of the motion tracker device, intensity of a light from the light array, wherein the additional optically isolated points are disposed at a distance from one another such that a variation in intensity of light due to shadowing effects from the plurality of light sources is different at the additional optically isolated points;
  generating, by the motion tracker device, a current signal representing a photodiode differential between the two additional optically isolated points and proportional to the intensity of the light; and
  transmitting, by the motion tracker device, the current signal to the computing device.

14. The method of claim 13, wherein the motion tracker device comprises:
  a second substrate; and
  at least a third light-direction detector and a fourth light-direction detector mounted on the second substrate at different locations such that an angle of incidence of light from the light array is different on the third and fourth light-direction detectors, the third and fourth light-direction detectors being mounted on the second substrate at an angle relative to the second substrate that is different from the angle of the light-direction detectors of the first and second light-direction detectors relative to the first substrate, and
  the first and second light-direction detectors being connected to the third and fourth plurality of light-direction detectors such that the second substrate is sandwiched between the two layers of light-direction detectors.

* * * * *